United States Patent
Thenuwara et al.

(10) Patent No.: US 9,352,149 B2
(45) Date of Patent: May 31, 2016

(54) RETENTION OF A MAGNET IN A COCHLEAR IMPLANT

(75) Inventors: Chuladatta Thenuwara, Valencia, CA (US); Mark B. Downing, Valencia, CA (US)

(73) Assignee: ADVANCED BIONICS AG, Staefa (CH)

( * ) Notice: Subject to any disclaimer, the term of this patent is extended or adjusted under 35 U.S.C. 154(b) by 43 days.

(21) Appl. No.: 14/344,200

(22) PCT Filed: Sep. 22, 2011

(86) PCT No.: PCT/US2011/052730
§ 371 (c)(1),
(2), (4) Date: Mar. 11, 2014

(87) PCT Pub. No.: WO2013/043176
PCT Pub. Date: Mar. 28, 2013

(65) Prior Publication Data
US 2014/0343626 A1    Nov. 20, 2014

(51) Int. Cl.
| | |
|---|---|
| A61N 1/00 | (2006.01) |
| A61N 1/08 | (2006.01) |
| A61N 1/375 | (2006.01) |
| A61N 1/36 | (2006.01) |
| A61N 1/372 | (2006.01) |
| B29C 45/14 | (2006.01) |
| B29K 83/00 | (2006.01) |
| B29L 31/00 | (2006.01) |

(52) U.S. Cl.
CPC .............. *A61N 1/08* (2013.01); *A61N 1/36032* (2013.01); *A61N 1/375* (2013.01); *A61N 1/37229* (2013.01); *B29C 45/14819* (2013.01); *B29K 2083/005* (2013.01); *B29K 2995/0008* (2013.01); *B29L 2031/753* (2013.01)

(58) Field of Classification Search
CPC . A61N 1/08; A61N 1/36032; A61N 1/37229; A61N 1/375
See application file for complete search history.

(56) References Cited

U.S. PATENT DOCUMENTS

| | | | |
|---|---|---|---|
| 6,178,353 | B1 | 1/2001 | Griffith et al. |
| 6,308,101 | B1 | 10/2001 | Faltys et al. |
| 6,542,777 | B1 | 4/2003 | Griffith et al. |
| 6,724,902 | B1 | 4/2004 | Shennib et al. |
| 7,976,453 | B2 | 7/2011 | Zimmerling |
| 8,013,699 | B2 | 9/2011 | Zimmerling |
| 8,255,058 | B2 | 8/2012 | Gibson et al. |
| 8,340,774 | B2 | 12/2012 | Hochmair et al. |
| 2002/0076071 | A1 | 6/2002 | Single |

(Continued)

FOREIGN PATENT DOCUMENTS

| | | |
|---|---|---|
| EP | 2119474 A2 | 11/2009 |
| EP | 2119474 A3 | 3/2010 |

(Continued)

*Primary Examiner* — Scott Getzow
(74) *Attorney, Agent, or Firm* — Fabian Vancott; Steven L. Nichols

(57) ABSTRACT

A system for retaining a magnet in a cochlear implant, comprising a retainer embedded within an encapsulant of the cochlear implant, and a magnet case engaged with the retainer. A retainer for retaining a magnet within a cochlear implant comprising a number of first fasteners that couple with a number of corresponding second fasteners of a magnet case hermetically sealing the magnet, and a number of supports embedded within an encapsulant of the cochlear implant.

25 Claims, 25 Drawing Sheets

(56) References Cited

U.S. PATENT DOCUMENTS

| | | |
|---|---|---|
| 2003/0181956 A1 | 9/2003 | Duncan et al. |
| 2004/0088051 A1 | 5/2004 | Seligman |
| 2005/0004629 A1 | 1/2005 | Gibson et al. |
| 2006/0030905 A1 | 2/2006 | Medina Malaver |
| 2007/0255349 A1 | 11/2007 | Torgerson et al. |
| 2008/0009920 A1 | 1/2008 | Gibson et al. |
| 2008/0221641 A1 | 9/2008 | Hochmair et al. |
| 2009/0099403 A1 | 4/2009 | Zimmerling |
| 2009/0287278 A1 | 11/2009 | Charvin |
| 2010/0274319 A1 | 10/2010 | Meskens |
| 2011/0224756 A1 | 9/2011 | Zimmerling et al. |
| 2011/0245891 A1 | 10/2011 | Fritsch et al. |
| 2012/0172659 A1 | 7/2012 | Ball et al. |
| 2012/0296155 A1 | 11/2012 | Ball |
| 2015/0087892 A1 | 3/2015 | Tourrel et al. |

FOREIGN PATENT DOCUMENTS

| | | |
|---|---|---|
| EP | 2117489 B1 | 5/2010 |
| EP | 2853287 A1 | 4/2015 |
| WO | 03092326 A1 | 11/2003 |
| WO | 2008089505 A1 | 7/2008 |
| WO | 2008109800 A1 | 9/2008 |
| WO | 2009048999 A1 | 4/2009 |
| WO | 2010000026 A1 | 1/2010 |
| WO | 2011011409 A1 | 1/2011 |
| WO | 2011011409 A8 | 1/2011 |
| WO | 2011075480 A2 | 6/2011 |

RETENTION OF A MAGNET IN A COCHLEAR IMPLANT

RELATED DOCUMENTS

The present application claims the benefit under 35 U.S.C. §371 to International PCT application No.: PCT/US2011/052730 filed Sep. 22, 2011 which application is incorporated herein by reference in its entirety.

BACKGROUND

Many people who are profoundly deaf have sensorineural hearing loss. This type of hearing loss can arise from the absence or the destruction of the hair cells in the cochlea that no longer transduce acoustic signals into auditory nerve impulses. Individuals with sensorineural hearing loss may be unable to derive significant benefit from hearing aid systems alone, no matter how loud the acoustic stimulus. This is because the natural mechanism for transducing sound energy into auditory nerve impulses has been damaged. Thus, in the absence of properly functioning hair cells, auditory nerve impulses cannot be generated directly from sounds.

To overcome sensorineural deafness, cochlear implant (CI) systems, or cochlear prostheses, have been developed that can bypass the hair cells located in the cochlea by presenting electrical stimulation directly to the auditory nerve fibers. This leads to the perception of sound in the brain and provides at least partial restoration of hearing function. Most of these cochlear prosthesis systems treat sensorineural deficit by stimulating the ganglion cells in the cochlea directly using an implanted electrode or lead that has an electrode array. Thus, a cochlear prosthesis operates by directly stimulating the auditory nerve cells, bypassing the defective cochlear hair cells that normally transduce acoustic energy into electrical activity in the connected auditory nerve cells.

External components of a CI system are removably coupled to the internal components of the CI system. Specifically, both the external components and the internal components include magnets. These magnets maintain a transmitter of the external components and an antenna of the internal components in position such that the transmitter and the antenna can communicate via electromagnetic transmission or optical transmission, among others, through the skin of the user. The internal magnet is held within a CI in the center of the antenna coil. When subjected to certain forces, such as impact forces from a fall or impact against hard object, or in the presence of a strong magnetic field during a magnetic resonance imaging (MRI) procedure, this internal magnet can dislodge from the CI or from portions of the CI, or can flip.

For example, an MRI device uses powerful magnetic fields to produce detailed images of internal structures of the human body, and is often used to image the head of a patient. If a user of a CI system were exposed to the magnetic fields produced by an MRI device, the magnet within the CI could dislodge from its original position, move within the body of the user, or flip due to the drastic and powerful change in the magnetic fields surrounding the CI.

In some cases, particularly when a relatively large magnetic field strength is used, a user of a CI system may need to undergo minor surgery to remove the magnet prior to an MRI procedure, and then endure a second surgery to reinstall the magnet after the MRI. These surgeries to remove and reinstall the magnet pose a risk of damage to the implant. These surgeries also require general anesthetic when performed on children, and subject the patient to risk of infection and breakdown of the skin overlying the CI due to the repeated surgeries.

Additional reasons to remove the magnet include preventing demagnetization of the internal magnet during MRI, replacing a magnet that has been demagnetized from one or more MRI procedures, replacing a magnet that has been otherwise damaged or dislodged, and eliminating artifacts on the MRI image caused by the internal magnet.

BRIEF DESCRIPTION OF THE DRAWINGS

The accompanying drawings illustrate various examples of the principles described herein and are a part of the specification. The examples are given merely for illustration, and do not limit the scope of the claims.

Throughout the drawings, identical reference numbers designate similar, but not necessarily identical, elements.

DETAILED DESCRIPTION

Figure 1:
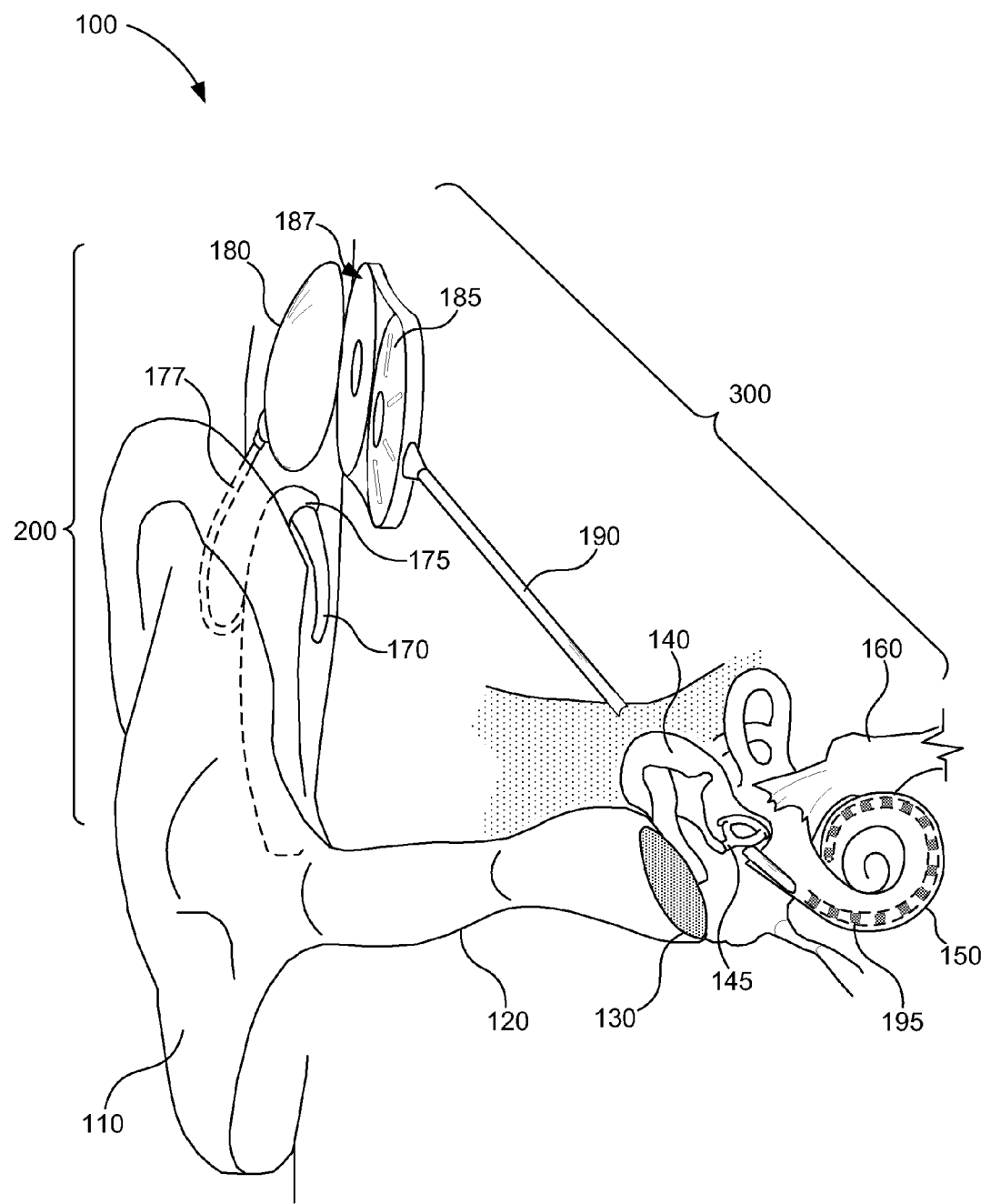
FIG. 1 is an illustrative diagram showing a CI system in use, according to one example of principles described herein.

Individuals with hearing loss can be assisted by hearing devices referred to as cochlear implants (CI). However, if a user is exposed to a magnetic field produced by an MRI device, the magnet within the internal components of the CI may dislodge from its original position, move within the body of the user, or flip due to the drastic and powerful change in the magnetic fields surrounding the CI system. Thus, exposure to the magnetic fields produced by an MRI device may cause injury to the user of a CI or may damage portions of the CI including a silicone pocket in which the magnet is enclosed. The present application discloses a system for retaining a magnet in a CI. The system comprises a retaining nest embedded within an encapsulant of the CI, and a magnet case removably engaged with the retaining nest. Several examples are disclosed below. Some of the examples described below may be used to ensure that a magnet in a CI does not dislodge from its original position, move within the body of the user, or flip due to magnetic fields produced within a low power MRI procedure. Other examples described below may be used to assist a clinician in removal and replacement of a magnet in a CI in conjunction with any power level MRI procedures including relatively higher-powered MRI procedures.

The present disclosure regarding CI may be similarly applied to other types of hearing aid systems. Other types of hearing aid system to which the present disclosure may apply include, for example, middle ear implants and acoustic implants.

As used in the present specification and in the appended claims, the term "magnet" is meant to be understood broadly as any material that produces a magnetic field. Some examples of magnets include a permanent magnet, ferromagnetic materials, a ferrite magnet, or a biocompatible magnet.

Further, as used in the present specification and in the appended claims, the terms "detachable," "removably engaged," or similar language is meant to be understood broadly as any first element that is connected to and disconnected from a corresponding second element within an associated device without disassembly or destruction of either the first or second elements.

Still further, as used in the present specification and in the appended claims, the terms "retainer," "nest," or similar language is meant to be understood broadly as any element within a cochlear implant (CI) that retains a magnet of the CI in an original position within the CI.

Even still further, as used in the present specification and in the appended claims, the term "a number of" or similar language is meant to be understood broadly as any positive number comprising 1 to infinity; zero not being a number, but the absence of a number.

In the following description, for purposes of explanation, numerous specific details are set forth in order to provide a thorough understanding of the present systems and methods. It will be apparent, however, to one skilled in the art that the present apparatus, systems, and methods may be practiced without these specific details. Reference in the specification to "an example" or similar language means that a particular feature, structure, or characteristic described in connection with that example is included as described, but may not be included in other examples.

An electrode array for implantation into the scala tympani typically comprises several separately connected stimulating electrodes, numbering about 6 to 30, longitudinally disposed on a thin, elongated, flexible carrier. The electrode array is pushed into the scala tympani duct in the cochlea, typically to a depth of about 8 to 30 mm via a cochleostomy or via a surgical opening made in the round window at the basal end of the duct.

In use, the cochlear electrode array delivers electrical current into the fluids and tissues immediately surrounding the individual electrode contacts to create transient potential gradients that, if sufficiently strong, cause the nearby auditory nerve fibers to generate action potentials. The auditory nerve fibers branch from cell bodies located in the spiral ganglion, which lies in the modiolus, adjacent to the inside wall of the scala tympani. The density of electrical current flowing through volume conductors such as tissues and fluids tends to be highest near the electrode contact that is the source of the current. Consequently, stimulation at one contact site tends to selectively activate those spiral ganglion cells and their auditory nerve fibers that are closest to that electrode.

FIG. 1 is a diagram showing an illustrative cochlear implant (CI) system (100) having a CI (300) with an electrode array (195) that is surgically placed within the patient's cochlea (150). In a properly functioning human ear, sound enters the external ear, or pinna, (110) and is directed into the auditory canal (120) where the sound wave vibrates the tympanic membrane (130). The motion of the tympanic membrane (130) is amplified and transmitted through the ossicular chain (140), which includes three bones in the middle ear. The third bone of the ossicular chain (140), the stapes (145), contacts the outer surface of the cochlea (150), and causes movement of the fluid within the cochlea (150). Cochlear hair cells respond to the fluid-borne vibration in the cochlea (150) and trigger neural electrical signals that are conducted from the cochlea to the auditory cortex via the auditory nerve (160).

As indicated above, the CI system (100) includes a surgically implanted electronic device that provides a sense of sound to a person who is profoundly deaf or severely hard of hearing. The CI system (100) operates by direct electrical stimulation of the auditory nerve cells, bypassing the defective cochlear hair cells that normally transduce acoustic energy into electrical energy.

External components (200) of the CI system can include a Behind-The-Ear (BTE) unit (175), which contains the sound processor and has a microphone (170), a cable (177), and a transmitter (180). The microphone (170) picks up sound from the environment and converts it into electrical impulses. The sound processor within the BTE unit (175) selectively filters and manipulates the electrical impulses and sends the processed electrical signals through the cable (177) to the transmitter (180). The transmitter (180) receives the processed electrical signals from the processor and transmits them to the implanted antenna (187) by, for example, electromagnetic transmission or optical transmission, among others.

The components of the CI (300) include an internal processor (185), an antenna (187), and a cochlear lead (190) having an electrode array (195). The internal processor (185) and antenna (187) are secured beneath the user's skin, typically above and behind the pinna (110).

The antenna (187) receives signals and power from the transmitter (180). The internal processor (185) receives these signals and performs a number of operations on the signals to generate modified signals. These modified signals are then sent along a number of signal wires that pass through the cochlear lead (190) and are individually connected to the electrodes in the electrode array (195). The electrode array (195) is implanted within the cochlea (150) and provides electrical stimulation to the auditory nerve (160).

The CI (300) stimulates different portions of the cochlea (150) according to the frequencies detected by the microphone (170), in a similar manner as a properly functioning ear would experience stimulation at different portions of the cochlea depending on the frequency of sound vibrating the liquid within the cochlea (150). This allows the brain to interpret the frequency of the sound as if the hair cells of the basilar membrane were functioning properly.

Figure 2:
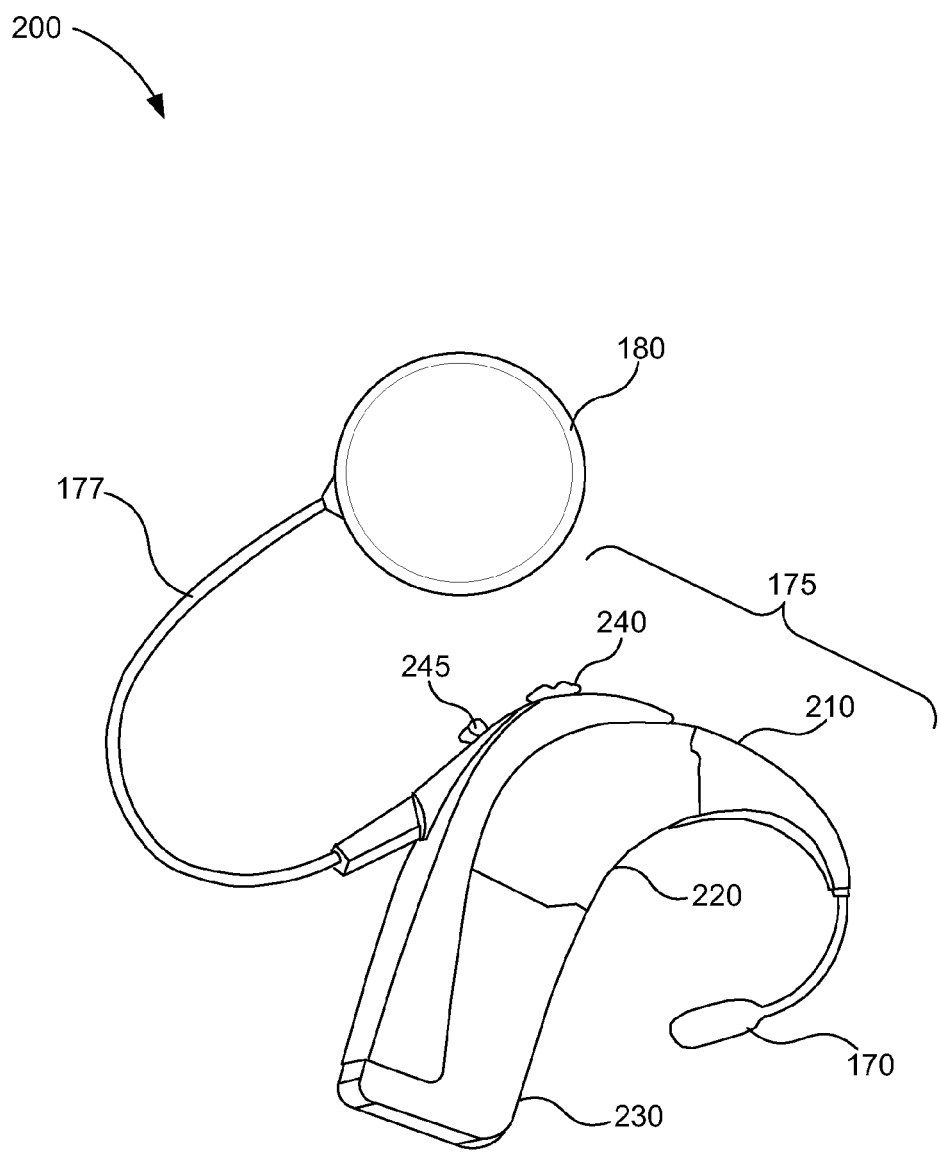
FIG. 2 is a diagram showing external components of an illustrative CI system, according to one example of principles described herein.

FIG. 2 is an illustrative diagram showing a more detailed view of the external components (200) of a cochlear implant (CI) system. External components (200) of the CI system include a BTE unit (175), which comprises a microphone (170), an ear hook (210), a sound processor (220), and a battery (230), which may be rechargeable. The microphone (170) picks up sound from the environment and converts it into electrical impulses. The sound processor (220) selectively filters and manipulates the electrical impulses and sends the processed electrical signals through a cable (177) to the transmitter (180). A number of controls (240, 245) adjust the operation of the processor (220). These controls may include a volume switch (240) and program selection switch (245). The transmitter (180) receives the processed electrical signals from the processor (220) and transmits these electrical signals and power from the battery (230) to the CI (300) by electromagnetic transmission.

Figure 3:
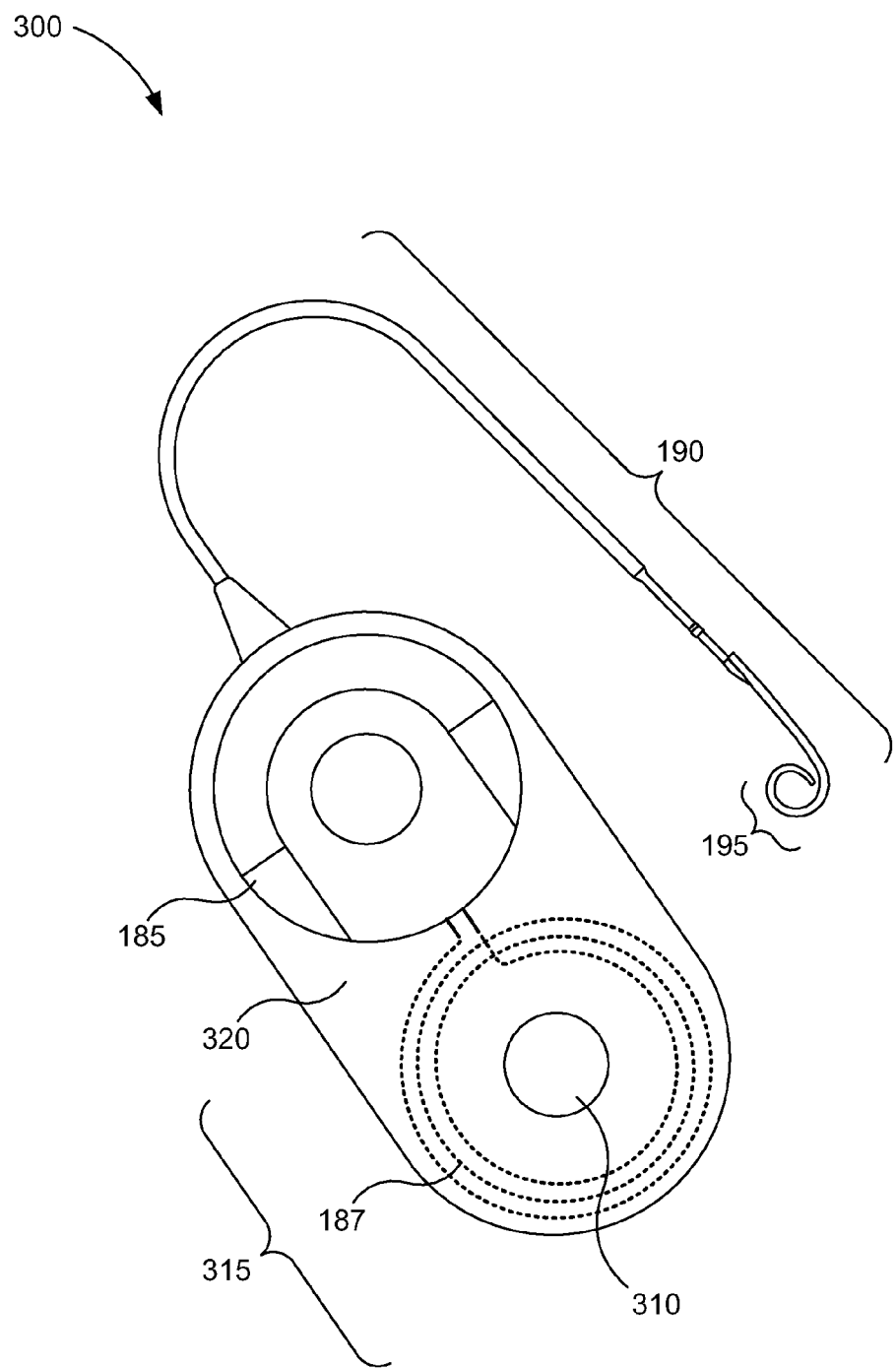
FIG. 3 is a diagram showing the internal components of an illustrative CI system, according to one example of principles described herein.

FIG. 3 is an illustrative diagram showing one example of a cochlear implant (CI) (300), including an internal processor (185), an antenna (187), and a cochlear lead (190) having an electrode array (195). The CI (300) is surgically implanted such that the electrode array (195) is internal to the cochlea, as shown in FIG. 1. The internal processor (185) and antenna (187) are secured within an encapsulant (320), and beneath the user's skin, typically above and behind the pinna (110), with the cochlear lead (190) connecting the internal processor (185) to the electrode array (195) within the cochlea. In one example, the encapsulant (320) is made of a polysiloxane, such as medical grade silicone, which completely surrounds the internal processor (185), antenna (187), and other elements, and separates any of these elements from human tissue so that these elements do not react with human tissues.

As discussed above, the antenna (187) receives signals from the transmitter (180) and sends the signals to the internal processor (185). The internal processor (185) modifies the signals and passes them along the appropriate wires to activate a number of the electrodes within the electrode array (195). This provides the user with sensory input that is a representation of external sound waves sensed by the microphone (170).

The CI (300) further includes a magnet (310) juxtaposed to the antenna (187). In one example, the magnet (310) is centered within the circular shape formed by the antenna (187). With the magnetic forces provided by the magnet (310), the transmitter (180) and the antenna (187) are communicatively coupled through the user's skin, and the transmitter (180) and the antenna (187) can then communicate via electromagnetic transmission. In one example, the transmitter (180) comprises a magnet or magnetic material to which the magnet (310) of the CI (300) is attracted.

As addressed above, if a user of a CI system (100) is exposed to the magnetic fields produced by an MRI device, the magnet (310) within the first portion (315) of the CI (300) may dislodge from its original position, or flip due to the drastic and powerful change in the magnetic fields surrounding the CI. A user is thus subjected to a risk of physical trauma to various tissues of his or her body as well as damage to the CI (300). Tissues of the user's body that may be traumatized may include the scalp and skull surrounding the first portion (315) of the CI (300).

Portions of the CI (300) that may be damaged if exposed to the magnetic fields produced by an MRI device include the encapsulant (320), the internal processor (185), the antenna (187), the cochlear lead (190), the electrode array (195), or other elements of the CI (300). For example, the magnet (310), if displaced by the magnetic field of the MRI device, could tear through the encapsulant (320) and expose other elements of the CI (300) to human tissues. This, in turn, may cause other elements of the CI (300) to degrade due to exposure to human tissues.

Figure 4:
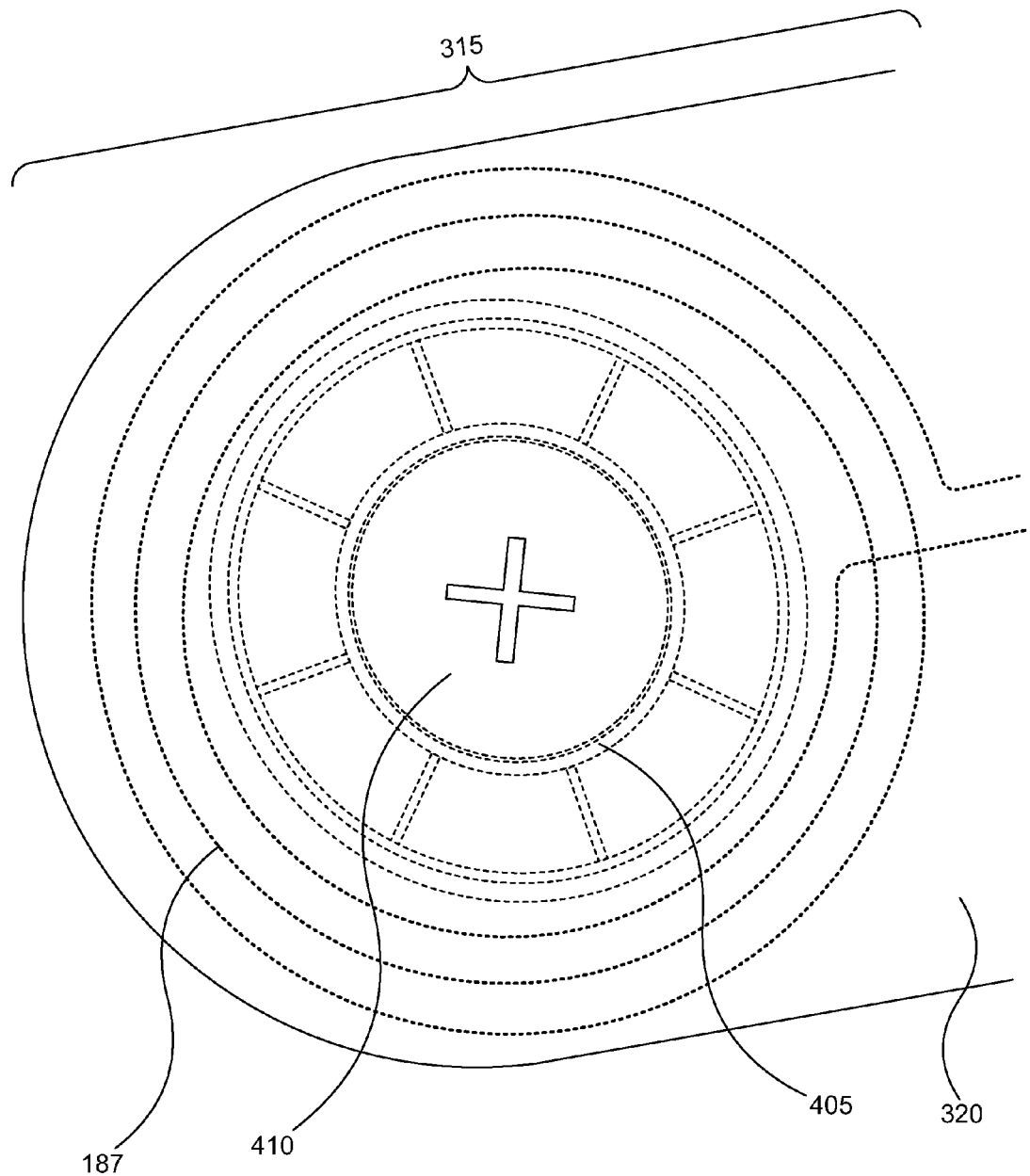
FIG. 4 is a perspective view of a first portion of a CI showing an embedded nest and a magnet case, according to one example of principles described herein.

In light of the above risks involved with performing an MRI procedure on a user of a CI (300), FIG. 4 is a perspective view of a first portion (315) of a CI (300) showing an embedded nest (405) and a magnet case (410), according to one example of principles described herein. The magnet case (410) is removably coupled to the embedded nest (405), as will be described in more detail below. The ability to selectively engage or disengage the magnet case (410) from the embedded nest (405) of the example of FIG. 4 and other examples described herein has several advantages. One such advantage includes a reduction in complexity of the surgery to remove the magnet from the CI (300) before performing an MRI procedure. The present disclosure makes the removal of the magnet case (410) relatively less invasive without the techniques.

Another advantage is that surgery does not have to be performed to remove the magnet case (410) when the user is exposed to certain levels of magnetic forces produced by the MRI device. If the user of the CI (300) is expected to be exposed to relatively low levels of magnetic forces during the MRI procedure, then the magnet case (410) does not have to be removed. This is because the embedded nest (405) that couples the magnet case (410) to the encapsulant (320) provides support for the magnet case (410) such that the magnet case (410) will not be displaced from the encapsulant (320) and the rest of the CI (300). Still another advantage lies in the fact that if the magnet (310) fails for any reason, such as by becoming demagnetized from repeat MRI, the magnet (310)

can be replaced without having to replace the entire CI (300). Other advantages exist, and will be disclosed and described below.

Another advantage of the example of FIG. 4 and other examples described herein is that if the user of the CI (300) is expected to be exposed to relatively low-strength magnetic fields produced by an MRI device, then the magnet (310) does not have to be removed from the CI (300). In this way, the user does not have to be subjected to a surgical procedure to remove the magnet (310). This is because the embedded nest (405) will retain the magnet (300) within the CI (300) and ensure that the magnet (310) does not move or flip due to these low level MRI procedures. Further, the user of the CI (300) may experience an impact to the head. If this is to occur to a user of the CI (300), the retainer or nest of the examples described herein will ensure that the magnet (310) does not move or become dislodged from the CI (300).

Turning again to FIG. 4, the embedded nest (405) is intricately coupled to the encapsulant (320). In one example, the encapsulant (320) is made of a polysiloxane such as, for example, silicone, as described above. In this example, a core pin is inserted within a nest (405) to keep the inner portion of the nest (405) open so that it will later accommodate the magnet case (410). The nest (405), with the core pin, is then inserted in a mold. Liquid silicone rubber (LSR) is injected into the mold through injection molding processes, and cured to form the encapsulant (320). Alternatively, other processes, such as transfer molding, compression molding, or casting, may be used. In one example, curing of the silicone is brought about by cross-linking the polymer chains of the polymerized silicone though the addition of a number of chemical additives, and exposure to ultraviolet radiation or heat.

In one example, the same injection molding and curing process is performed simultaneously for other elements of the CI (300) including, for example, the antenna (187), the internal processor (185), and the cochlear lead (190), among other elements. In another example, the magnet case (410) is engaged with the embedded nest (405) during the curing of the silicone so that the void (535) defined within the embedded nest (405) does not fill with pre-cured liquid silicone polymer, and so that a tight fit may be provided for the magnet case (410) within the silicone.

Figure 5:
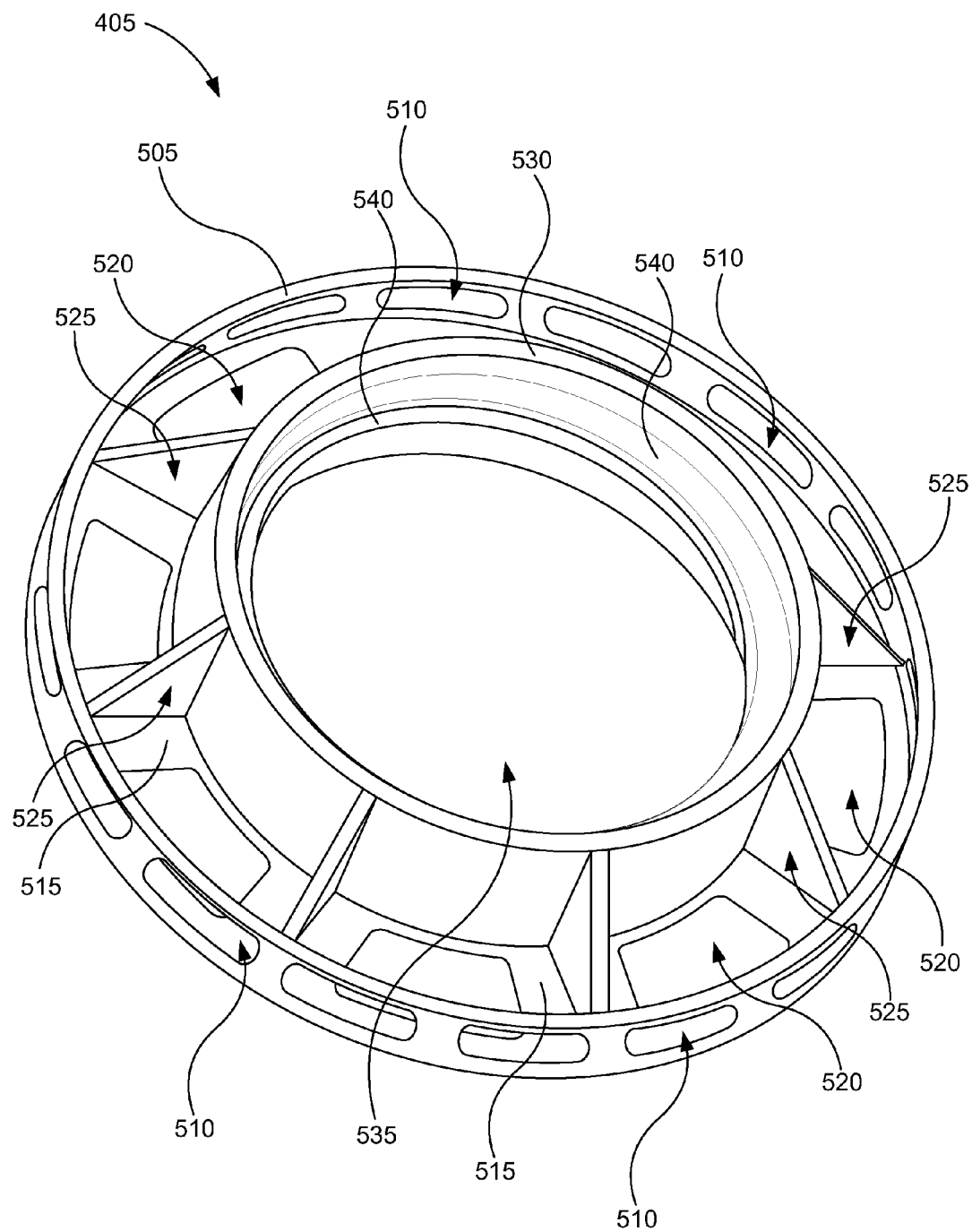
FIG. 5 is a perspective view of the nest of FIG. 4, according to one example of principles described herein.

FIG. 5 is a perspective view of the embedded nest (405) of FIG. 4, according to one example of principles described herein. The embedded nest (405) is made of any rigid material that can securely retain the magnet case (410) within the first portion (315) of the CI (300) when the magnet case (410) is exposed to magnetic forces provided by an MRI device. In one example, the embedded nest (405) is made of a thermoplastic material such as, for example, polyether ether ketone (PEEK) or a polysulfone.

The embedded nest (405) may comprise any number of features and surfaces that serve to secure the encapsulant (FIG. 4, 320) to the embedded nest (405) and allows the embedded nest (405) to secure the magnet case (410) within the CI (300). In one example, the embedded nest (405) comprises an outer ring (505) including a number of outer ring voids (510) defined therein. The outer ring voids (510) are provided to allow for the encapsulant (320) of the CI (300), when formed around the embedded nest (405), to couple with the embedded nest (405) during curing of the silicone polymer, as described above. The outer ring (505) allows for increased surface area to which the magnet case (410) can anchor.

The embedded nest (405) further comprises a base (515) defining a number of base voids (520). The base voids (520) are provided to allow for the encapsulant (320) of the CI (300) to couple with the embedded nest (405) during curing of the silicone polymer, as described above. The embedded nest (405) also includes a number of buttresses (525). The buttresses (525) assist in providing support throughout the embedded nest (405) and serve as another element within the embedded nest (405) to which the encapsulant (320) of the CI (300) can couple.

An inner ring (530) is coaxially formed with respect to the outer ring (505). The inner ring (530) defines a void (535) within the embedded nest (405) in which the magnet case (410) is seated and to which the magnet case (410) is coupled. The inner ring (530) includes a number of female threads (540). The female threads (540) mate with a number of male threads located on the magnet case (410), and secure the magnet case (410) to the embedded nest (405), as will be described in more detail below. In one example, the female threads (540) include double female half-turn threads that mate with double male half-turn threads included on the magnet case (410).

Figure 6:
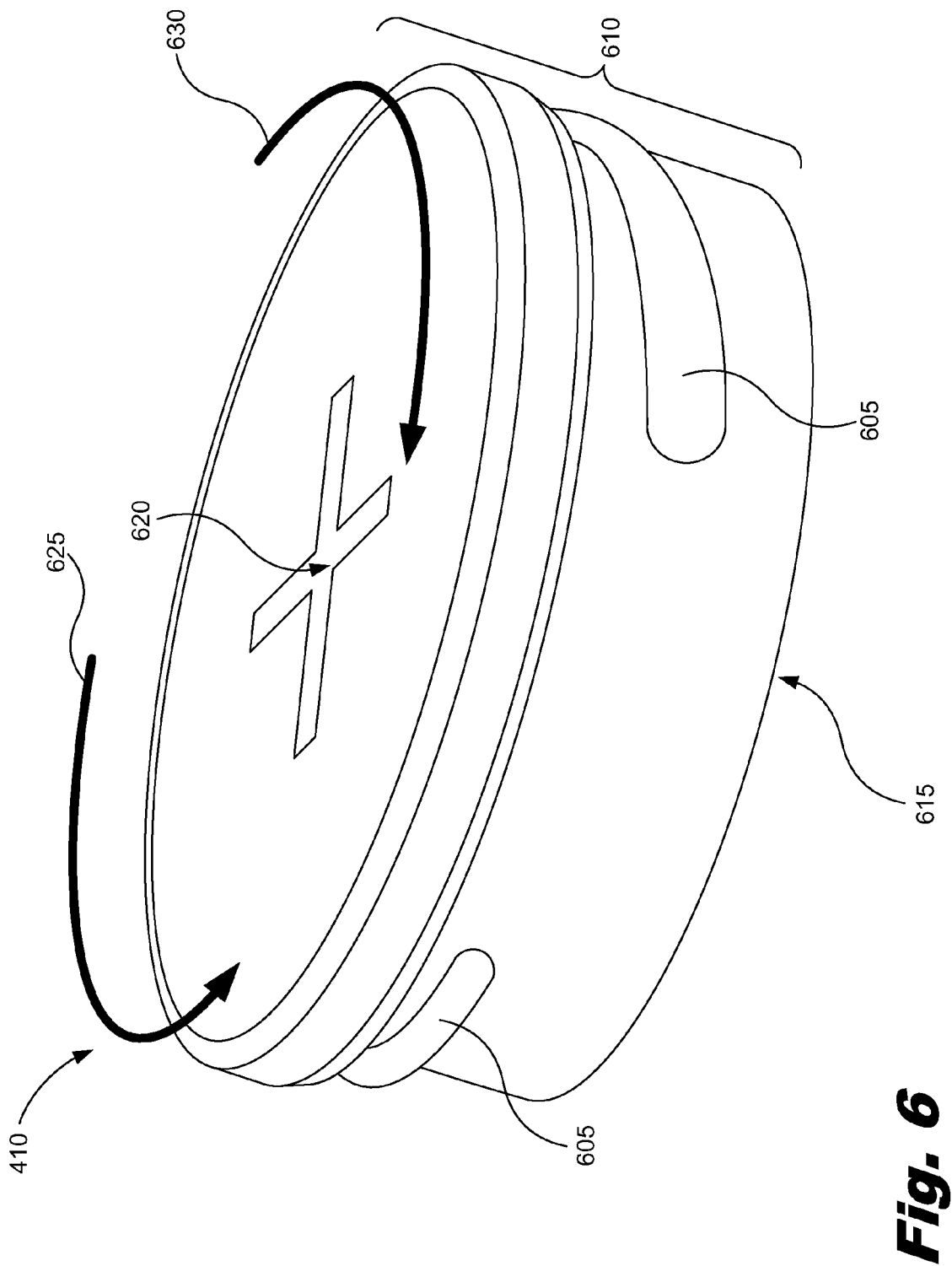
FIG. 6 is a perspective view of magnet case of FIG. 4, according to one example of principles described herein.

Turning now to FIG. 6, a perspective view of magnet case (410) of FIG. 4, according to one example of principles described herein, is depicted. The magnet case (410) houses the magnet (310), secures the magnet to the embedded nest (405), and ensures that the magnet (310) is not exposed to human tissue when implanted within the user's body. Thus, the magnet case (410) is made of a material that does not interact with human tissues. In one example, the magnet case (410) is made of, for example, titanium (Ti) or a titanium alloy.

The magnet case (410) comprises a top portion (610) which forms a cavity, and a bottom cap (615) that closes the cavity. A magnet (310) is placed inside the cavity, and the bottom cap (615) is welded to the top portion (610). In this manner, the magnet is hermetically sealed within the magnet case (410). Hermetically sealing the magnet (310) in a housing prevents the magnet from interacting with human tissues while implanted in the user.

As discussed above, the magnet case (410) can be removably coupled to the embedded nest (405) using a number of male threads (605) that mate with the female threads (540) of the embedded nest (405). Further, as discussed above, the male threads (605) comprise, for example, double male half-turn threads that mate with double female half-turn threads positioned on the embedded nest (405).

The magnet case (410) further includes an extraction cavity (620). In one example, the extraction cavity (620) is formed and defined within the top portion (610) of the magnet case (410). A tool is provided that mates with the extraction cavity (620) so that a clinician can remove the magnet case (410) and magnet (310) from the cochlear implant (CI) (300) prior to an MRI procedure, for example. The clinician, after surgically accessing the CI (300), can selectively engage or disengage the magnet case (410) with or from the embedded nest (405) by turning the magnet case (410) with the tool in the direction of the arrows (625, 630). In one example, the engagement of the magnet case (410) with the embedded nest (405) is achieved by turning the magnet case (410) in the direction of arrow (630). Likewise, in this example, disengagement of the magnet case (410) with the embedded nest (405) is achieved by turning the magnet case (410) in the direction of arrow (625). The above-mentioned tool will be discussed in more detail below in connection with FIG. 8.

In assisting the removal of the magnet case (410) from the embedded nest (405), a spring force (725) is provided between the encapsulant (320) and the bottom of the magnet case (410). The spring force (720) provides force in an axial direction with respect to the magnet case (410) as indicated by arrow (720). In one example, the spring force (720) is provided by the encapsulant (320). In this example, as the silicone of the encapsulant (320) is formed around the embedded nest (405), additional silicone may be provided at the bottom of the void (535) within the embedded nest (405). This additional silicone, having a restoring force, provides the spring force (725) to act against the magnet case (410). One advantage of including the additional silicone is that this axial force (720) locks the magnet case (410) within the embedded nest (405) when engaged with the embedded nest (405). The axial force (720) can be overcome by providing a force in the opposite direction of the axial force (720). Another advantage that the axial force (720) supplied by the additional silicone is that once the magnet case (410) is disengaged from the embedded nest (405), the magnet case (410) will be pushed out of the embedded nest (405) so that a clinician can readily grip the magnet case (410) and pull it from the CI (300).

In another example, a spring is embedded within the encapsulant (320) at bottom of the void (535) within the embedded nest (405), or, in another example, at the bottom of the magnet case (410). In a similar fashion, the spring locks the magnet case (410) in the embedded nest (405), and assists a clinician in removing the magnet case (410) from the CI (300). The above examples of incorporating a spring force into the encapsulant (320) of a CI (300) may be applied to other examples described below.

Figure 7:
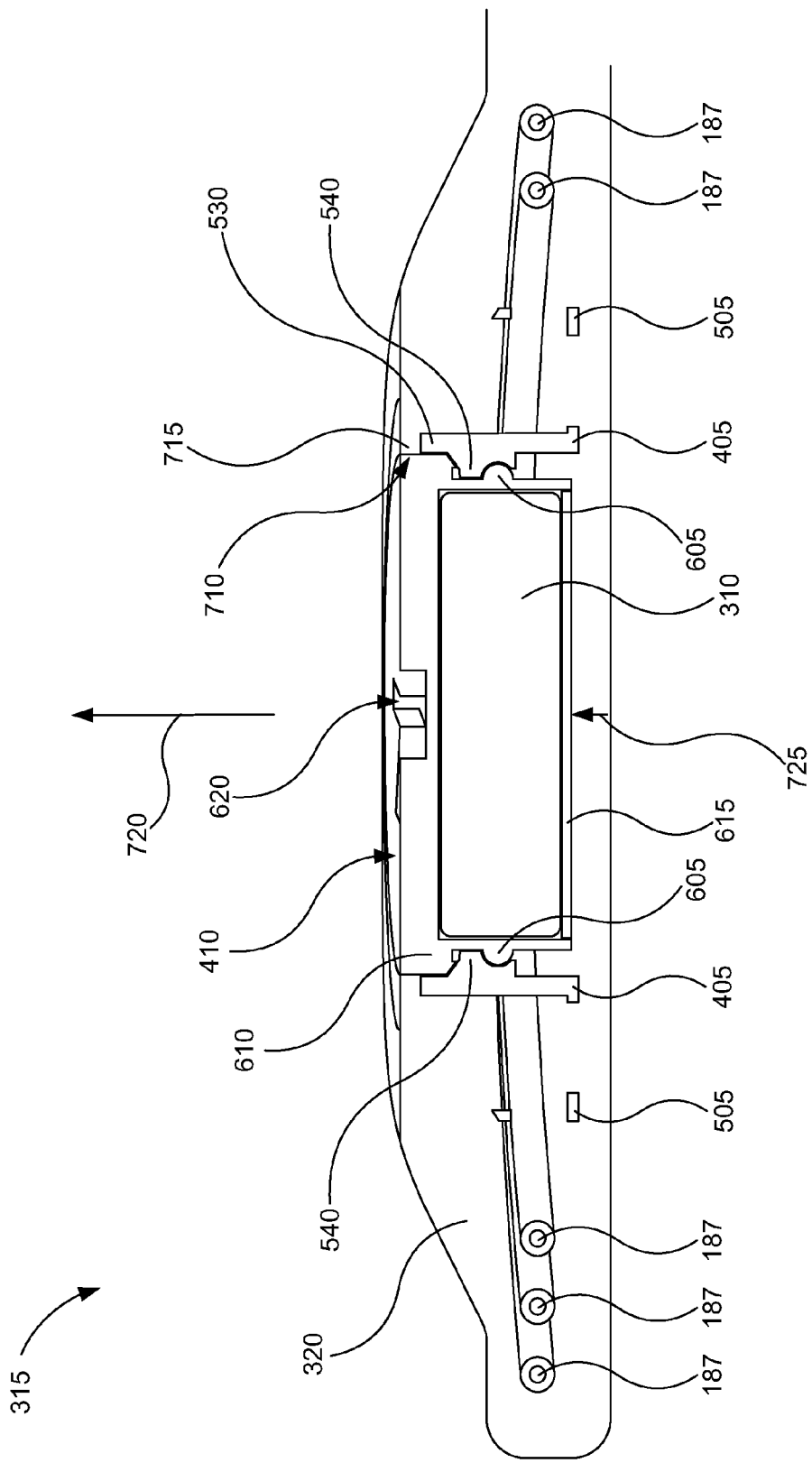
FIG. 7 is a cross-sectional diagram of the first portion of the CI of FIG. 4, according to one example of principles described herein.

Having described the various elements of the first portion (315) of the cochlear implant (CI) (300), their interaction with each other will now be described in more detail in connection with FIG. 7. FIG. 7 is a cross-sectional diagram of the first portion (315) of the CI (300) of FIG. 4, according to one example of principles described herein. FIG. 7 depicts the magnet case (410) with the magnet (310) hermetically sealed therein, and engaged with the embedded nest (405). The nest (405) is embedded within the encapsulant (320) along with the antenna (187).

In one example, the magnet case (410), when engaged with the embedded nest (405), protrudes from the embedded nest (405) to a degree as indicated by arrow (710). In this example, the encapsulant (320) creates a sealing lip (715) around the magnet case (410). The sealing lip (715) ensures that human tissues and other foreign objects do not enter the housing (410) and interact with the various elements of the first portion (315) of the CI (300). In another example, the sealing lip (715) extends over a portion of the top portion (610) of the magnet case (410). This example creates a larger seal around the magnet case (410).

Figure 8:
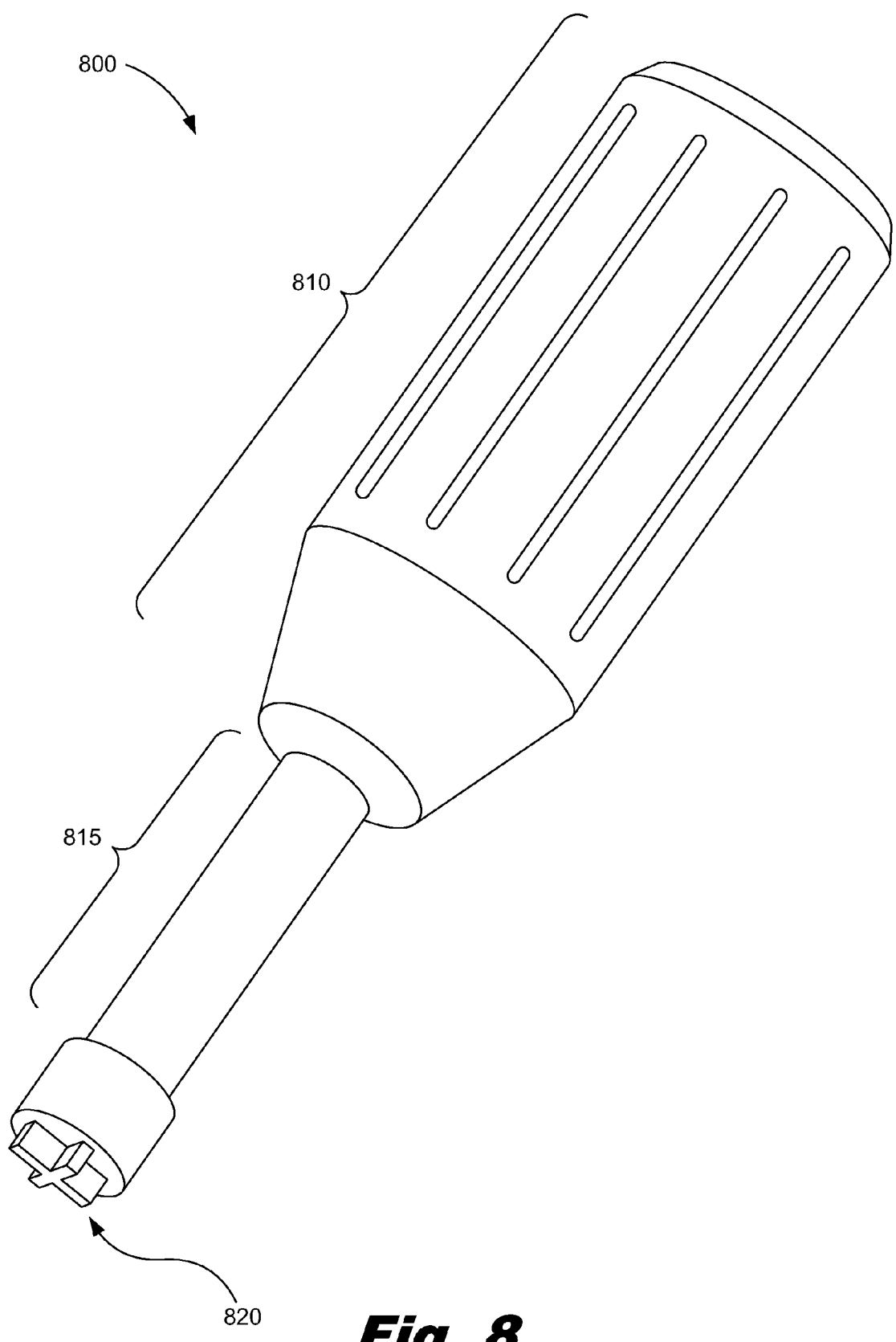
FIG. 8 is a perspective view of a magnet case removal tool for use in removing the magnet case of FIG. 4, according to one example of principles described herein.

As described above, a tool may be used to decouple the magnet case (410) from the embedded nest (405). FIG. 8 is a perspective view of a magnet case removal tool (800) for use in removing the magnet case (410) of FIG. 4, according to one example of principles described herein. The tool (800) includes a handle (810) for gripping by a clinician. A shaft (815) is coupled to the handle (810) for providing torque to an extraction bit (820). The extraction bit (820) is shaped to mate with the extraction cavity (620) of the magnet case (410). The extraction bit (820) and extraction cavity (620) have a matching shape. In one example, the extraction bit (820) and extraction cavity (620) have a shape similar to a plus sign. However, the mating shape between the extraction bit (820) of the tool (800) and the extraction cavity (620) of the magnetic housing (410) may be any shape including, for example, a square, a hexogon (hex), a pentagon, a slot, a Phillips shape, and a Frearson shape, among others.

In one example, the extraction bit (820) of the magnet case removal tool (800) is made of a magnetic material. In this example, the material may be any material that is attracted to a magnetic field, or any material that produces a magnetic field. Thus, in this example, the extraction bit (820) assists a clinician in installing and removing the magnet case (410, 1000) from the CI (300) during such procedures.

Figure 9:
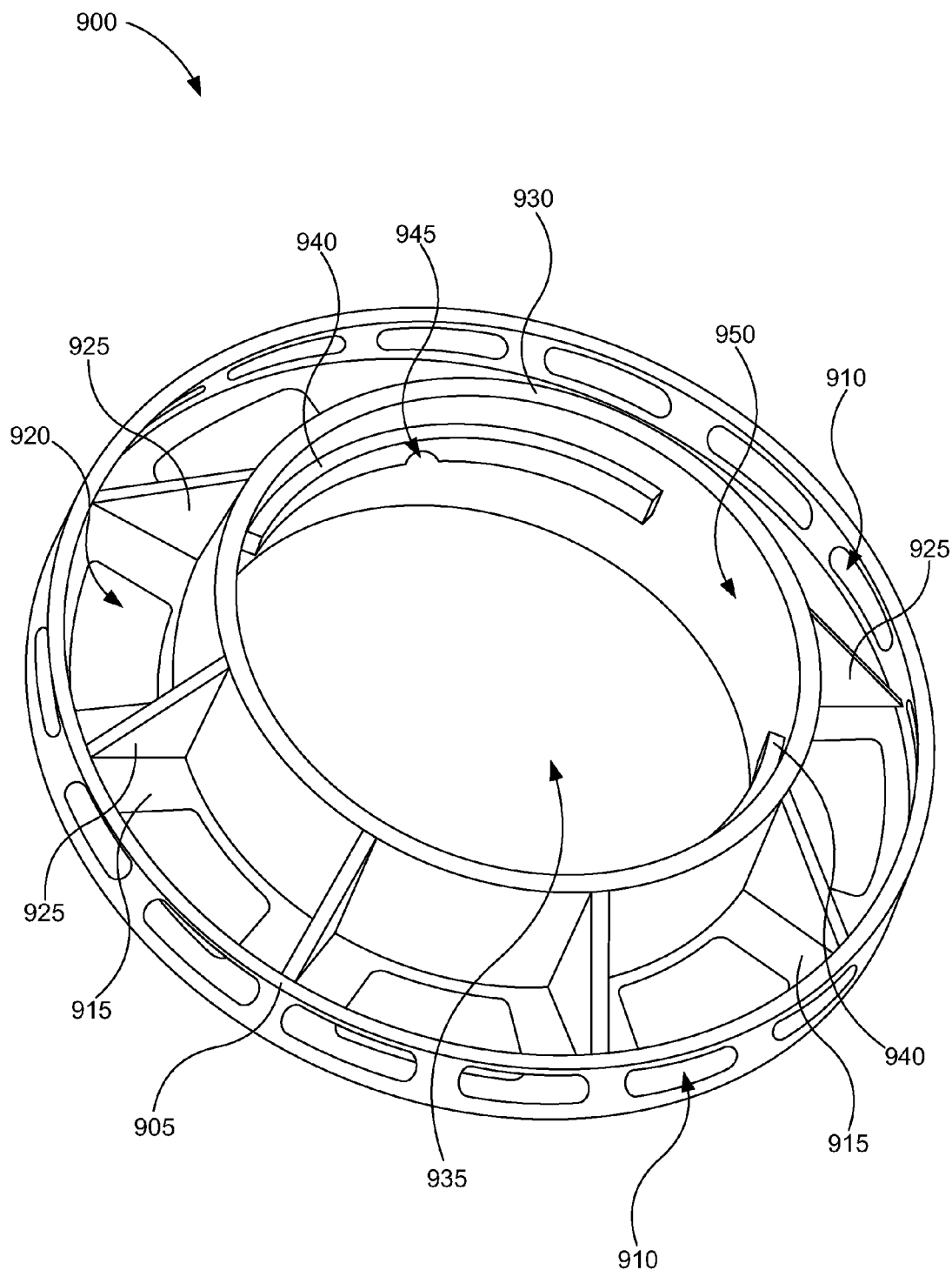
FIG. 9 is a perspective view of a nest, according to another example of principles described herein.
Figure 10:
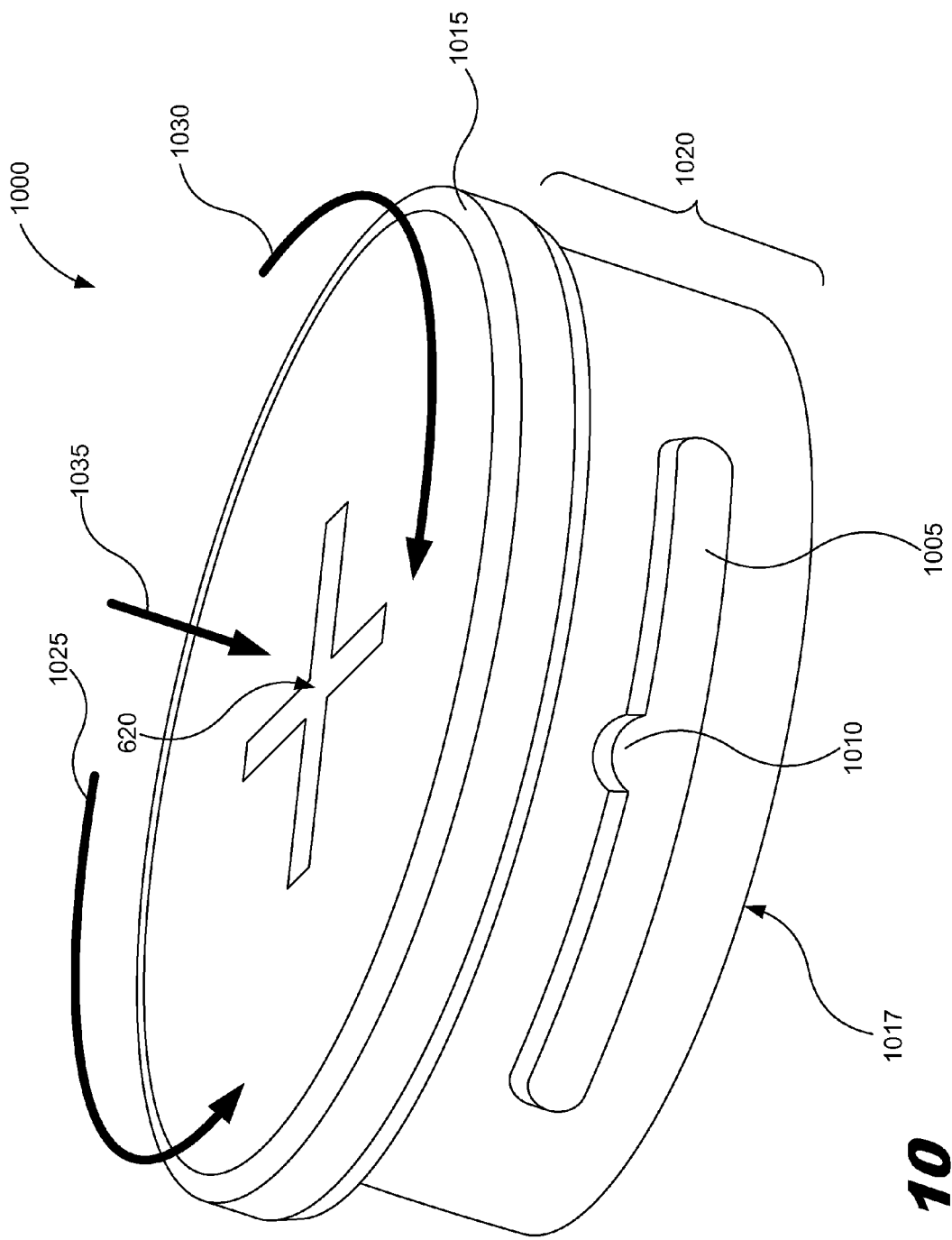
FIG. 10 is a perspective view of a magnet case for use in connection with the nest of FIG. 9, according to another example of principles described herein.
Figure 11:
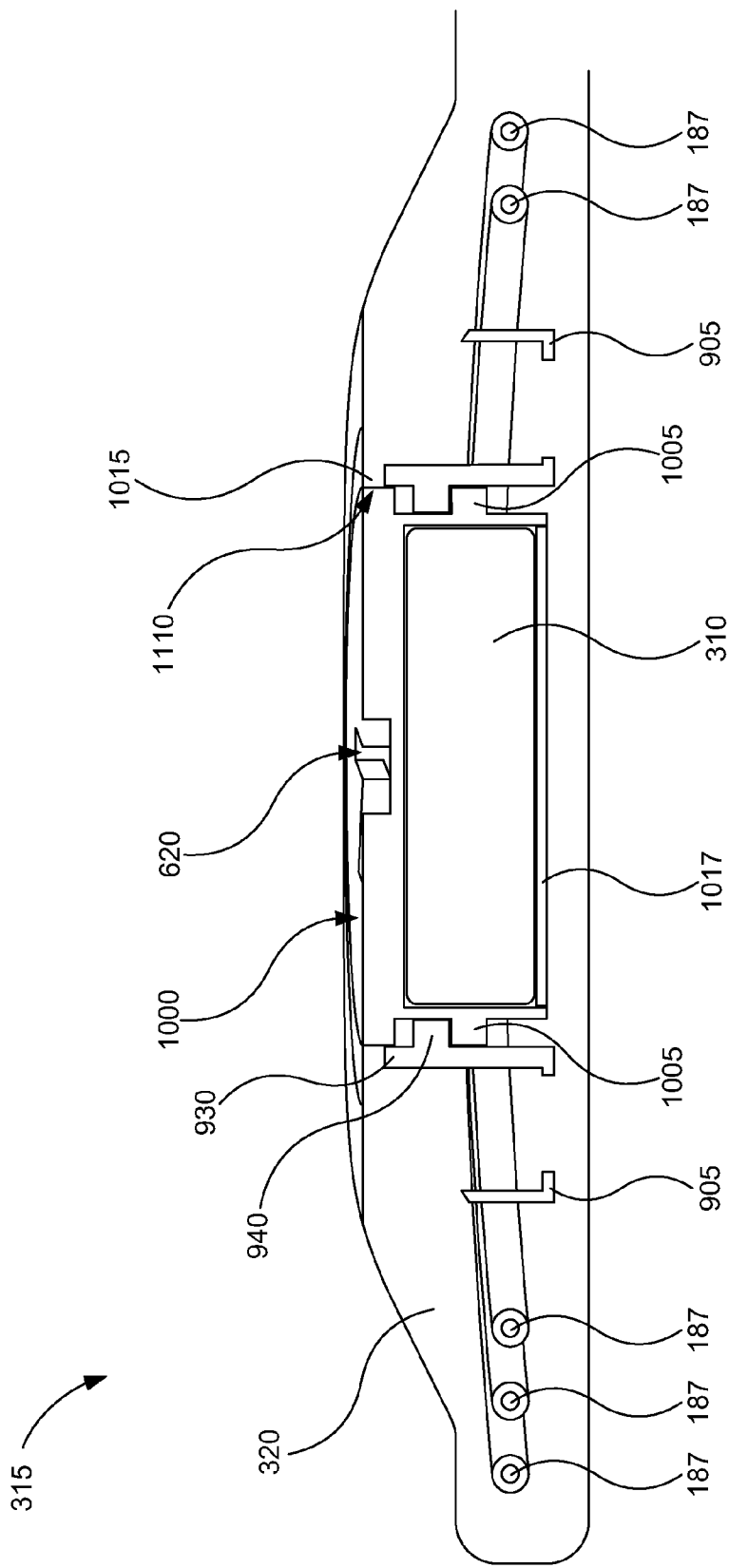
FIG. 11 is a cross-sectional diagram of the first portion of the CI depicting the embedded nest of FIG. 9 and the magnet case of FIG. 10, according to another example of principles described herein.

Turning now to FIGS. 9 through 11, another example of the first portion (315) of the cochlear implant (CI) (300) is disclosed. FIG. 9 is a perspective view of a nest (900), according to another example of principles described herein. The embedded nest (900) of FIG. 9 is made of similar material as the embedded nest (405) of FIGS. 4, 5, and 7. Further, the embedded nest (900) comprises any number of features and surfaces that serve to secure the housing (FIG. 4, 320) to the embedded nest (900) and allows the embedded nest (900) to secure the magnet case (FIG. 10, 1000) within the CI (300). In one example, the embedded nest (900) comprises an outer ring (905) including a number of outer ring voids (910) defined therein. The outer ring voids (910) are provided to allow for the encapsulant (320) of the CI (300) to couple with the embedded nest (900) during curing of the silicone polymer, as described above. The outer ring (905) allows for increased surface area to which the magnet case (FIG. 10, 1000) can anchor.

The embedded nest (900) further comprises a base (915) defining a number of base voids (920). The base voids (920) are provided to allow for the encapsulant (320) of the CI (300) to couple with the embedded nest (900) during curing of the silicone polymer, as described above. The embedded nest (900) also includes a number of buttresses (925). The buttresses (925) assist in providing support throughout the embedded nest (900) and serve as another element within the embedded nest (905) to which the encapsulant (320) of the CI (300) can couple.

An inner ring (930) is coaxially positioned with respect to the outer ring (905). The inner ring (930) defines a void (935) within the embedded nest (900) in which the magnet case (FIG. 10, 1000) is seated and to which the magnet case (FIG. 10, 1000) is coupled. The inner ring (930) includes a number of protrusions (940). The protrusions (940) include a number of notches (945). The notches (945) mate with a number of detents (FIG. 10, 1010) located on wings (FIG. 10, 1005) of the magnet case (FIG. 10, 1000), as will be discussed in more detail in connection with FIG. 10. In one example, the protrusions (940) include one notch (945) per protrusion (940). In another example, the protrusions (940) include more than one notch (945) per protrusion (940).

The protrusions (940) of the inner ring (930) do not extend the entire distance around the inner ring (930). Under this configuration, a number of spaces (950) along the inner ring (930) are void of a protrusion (940). This is so that the wings (FIG. 10, 1005) of the magnet case (FIG. 10, 1000) can enter between the protrusions (940), and be engaged below the protrusions (940). The magnet case (FIG. 10, 1000) will now be described in more detail.

FIG. 10 is a perspective view of a magnet case (1000) for use in connection with the embedded nest (900) of FIG. 9, according to another example of principles described herein. As similarly described above in connection with the magnet case (410) of FIGS. 4, 6, and 7, the magnet case (1000) of FIG. 10 houses the magnet (310), secures the magnet to the cochlear implant (CI) (300) via the embedded nest (900), and ensures that the magnet (310) is not exposed to human tissue when implanted within the user's body. Thus, the magnet case (1000) is made of a resilient material that does not interact with human tissues. In one example, the magnet case (1000) is made of, for example, titanium (Ti) or a titanium alloy.

The magnet case (1000) hermetically seals the magnet (310) through various processes as described above in connection with the magnet case (410) of FIGS. 4, 6, and 7. The magnet case (1000) comprises a number of wings (1005). The wings (1005) include a number of detents (1010) that match and mate with the notches (945) defined within the protrusions (940) of the embedded nest (900). In this manner, the magnet case (1000) is removably coupled to the embedded nest (900) using the number of notches (945) defined within the protrusions (940) of the embedded nest (900) that mate with the number of detents (1010) of the wings (1005).

A tool such as magnet case removal tool (800) is provided that mates with the extraction cavity (620) so that a clinician can remove the magnet case (1000) and magnet (310) from the embedded nest (900). The clinician, after surgically accessing the CI (300), can selectively engage or disengage the magnet case (1000) from the embedded nest (900). This is performed by pushing the magnet case (1000) down in the direction of arrow (1035) to disengage the detents (1010) from the notches (945). The magnet case (1000) is then turned with the tool in the direction of either of the arrows (1025, 1030). Once the wings (1005) of the magnet case (1000) are aligned with the number of lengths (950) along the inner ring (930) that are void of a protrusion (940), the wings (1005) can pass by the protrusions (940) and through the lengths (950). In this manner, the magnet case (1000) is decoupled from the embedded nest (900).

Having described the various elements of the first portion (315) of the cochlear implant (CI) (300) of this additional example, their interaction with each other will now be described in more detail in connection with FIG. 11. FIG. 11 is a cross-sectional diagram of the first portion (315) of the CI (300) depicting the embedded nest (900) of FIG. 9 and the magnet case (1000) of FIG. 10, according to another example of principles described herein. FIG. 10 depicts the magnet case (1000) with the magnet (310) hermetically sealed therein, and engaged with the embedded nest (900). The engagement of the magnet case (1000) with the embedded nest (900) is achieved via the mating of the detents (1010) of the wings (1005) with the notches (945) defined within the protrusions (940). The embedded nest (900) is contained within the encapsulant (320) along with the antenna (187).

In one example, the magnet case (1000), when engaged with the embedded nest (900), protrudes from the embedded nest (900) to a degree as indicated by arrow (1110). In this example, the encapsulant (320) creates a sealing lip (1015) around the magnet case (1000), as similarly disclosed above in connection with FIG. 7.

Figure 12:
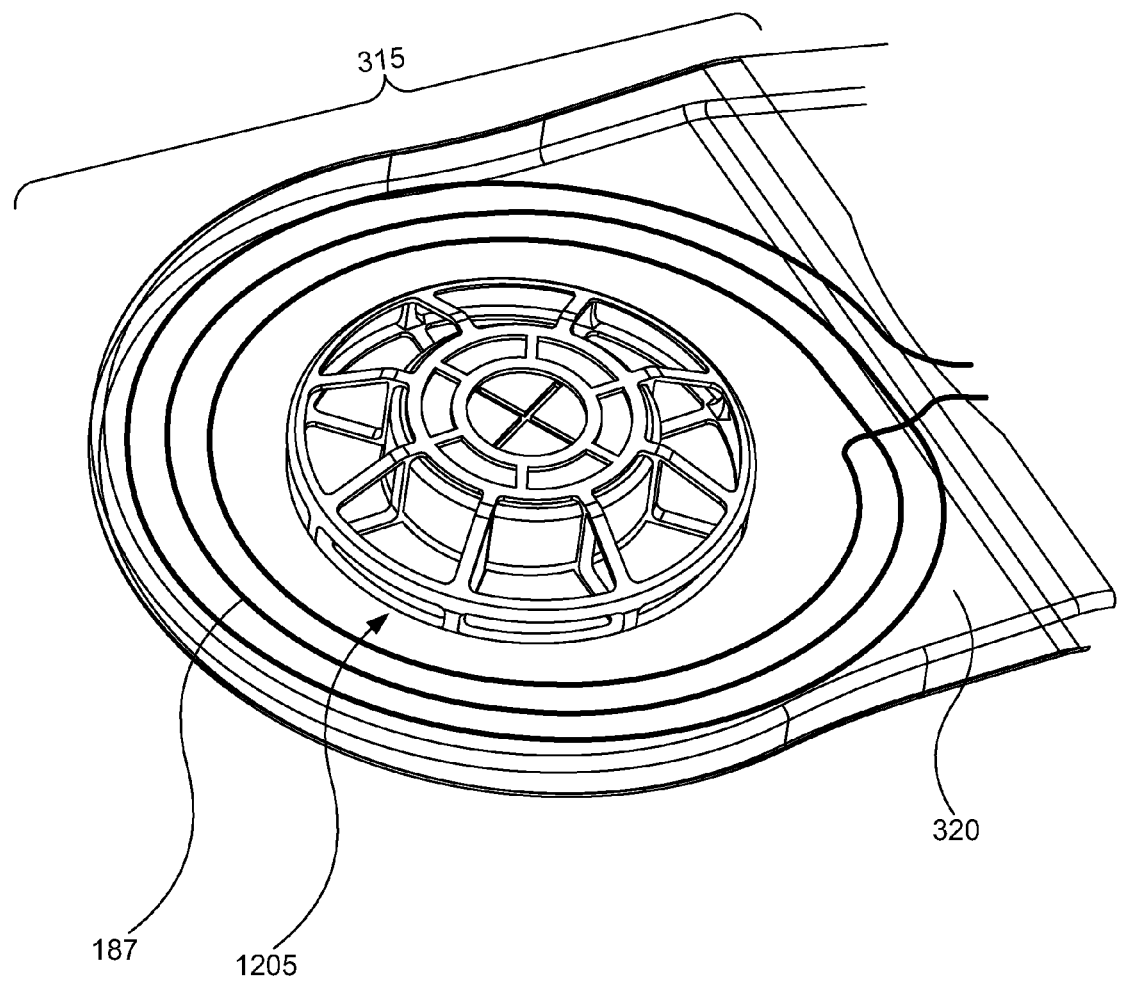
FIG. 12 is a perspective view of a first portion of a CI showing an embedded nest and a magnet, according to still another example of principles described herein.
Figure 13:
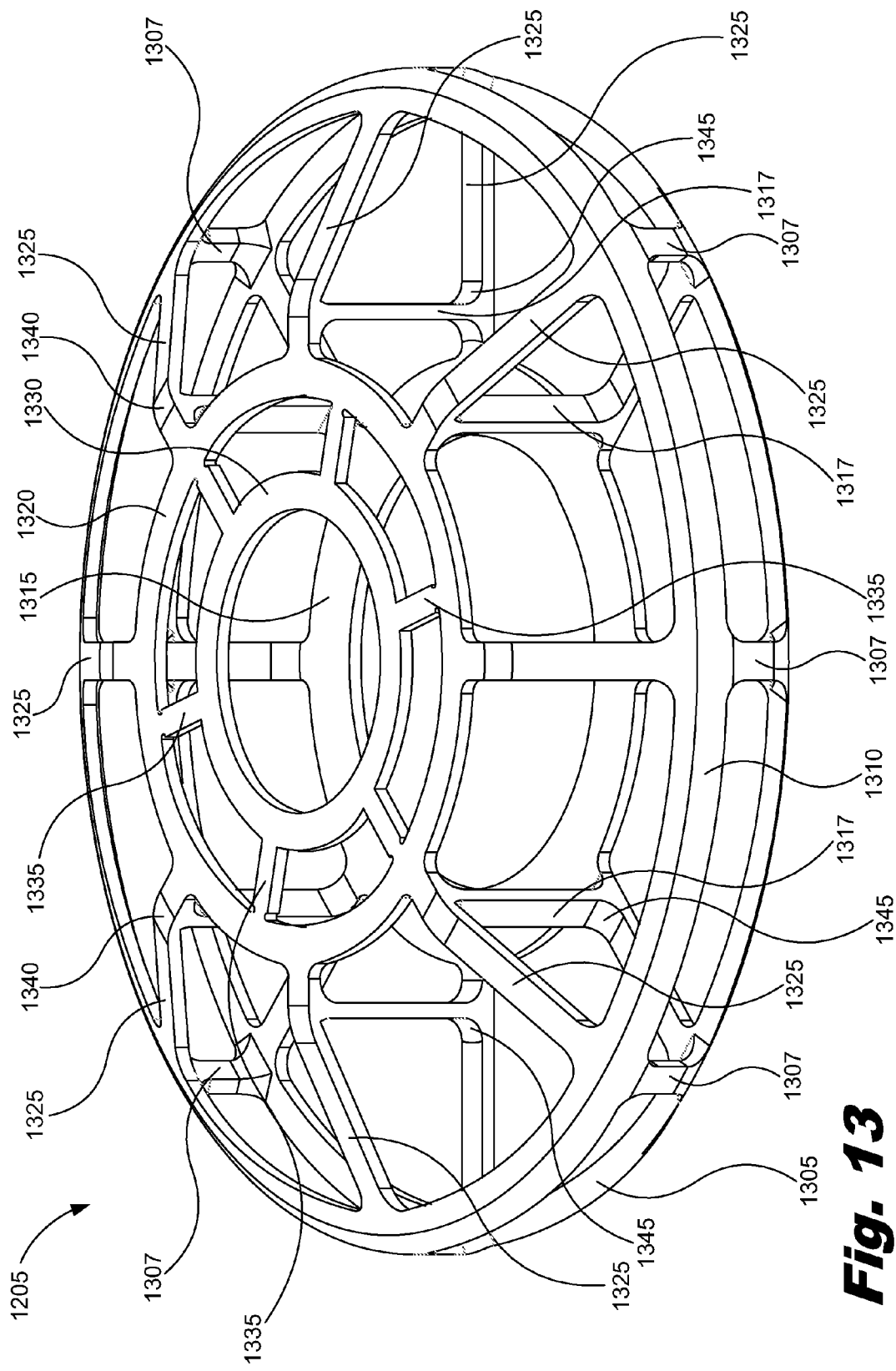
FIG. 13 is a perspective view of the nest of FIG. 12, according to still another example of principles described herein.

FIG. 12 is a perspective view of a first portion (315) of a cochlear implant (CI) (300) showing an embedded nest (1205) and a magnet (310), according to still another example of principles described herein. FIG. 13 is a perspective view of the embedded nest (1205) of FIG. 12. As depicted in FIG. 12, the embedded nest (1205) is embedded within the encapsulant (320) of the CI (300). Similarly, the antenna (187) is also embedded in the encapsulant (320).

As depicted in FIG. 13, the nest (1205) comprises a first outer ring (1305) and a second outer ring (1310), and a first inner ring (1315) and a second inner ring (1320). The first and second outer rings (1305, 1310) and first and second inner rings (1315, 1320) are coupled via a number of rib sections (1325). The rib sections (1325) create surfaces to which the encapsulant (320) couples. The first inner ring (1315) and a second inner ring (1320) are coupled via a number of inner braces (1317). Similarly, the first outer ring (1305) and a second outer ring (1310) are coupled via a number of outer braces (1307).

The embedded nest (1205) further comprises a magnet retention ring (1330). The magnet retention ring (1330) is coupled to the second inner ring (1320) by a number of retention ring supports (1335). The magnet retention ring (1330) retains a magnet (310) or a magnet case (410, 1000) containing a magnet (310) within the embedded nest (1205). In this manner, the magnet (310) is retained within the CI (300).

The embedded nest (1205) is made of any rigid material that can securely retain a biocompatible magnet (310) or a magnet case (410, 1000) containing a magnet (310) when exposed to magnetic forces provided by an MRI device. In one example, the embedded nest (405) is made of a thermoplastic material such as, for example, polyether ether ketone (PEEK) or a polysulfone. Each of the rib sections (1325) of the embedded nest (1205) further comprise a number of upper break points (1340) and lower break points (1345) at which the rib sections (1325) may be broken. Thus, the material from which the embedded nest (1205) is made can also be pre-stressed and engineered to break at the pre-stressed break points (1340).

With regard to the embedded nest (1205) of FIGS. 12 and 13, the embedded nest (1205) will retain the magnet (310) or a magnet case (410, 1000) containing the magnet (310) within the CI (300) during MRI procedures that utilize magnetic fields of relatively lower strength. However, when a user of a CI (300) is to be exposed to an MRI device that will produce magnetic fields of relatively higher strength, the magnet (310) or a magnet case (410, 1000) containing a magnet (310) can still be removed.

In one example, the removal of the magnet (310) or a magnet case (410, 1000) containing the magnet (310) may be achieved by a clinician surgically accessing the CI (300). The clinician then breaks or cuts the break points (1340, 1345) of the rib sections (1325), and removes the magnet (310) or a magnet case (410, 1000) containing the magnet (310) along with the first and second inner rings (1315, 1320), magnet retention ring (1330), and retention ring supports (1335). In this manner, the user of the CI (300) can have a relatively high power MRI procedure performed.

Figure 14:
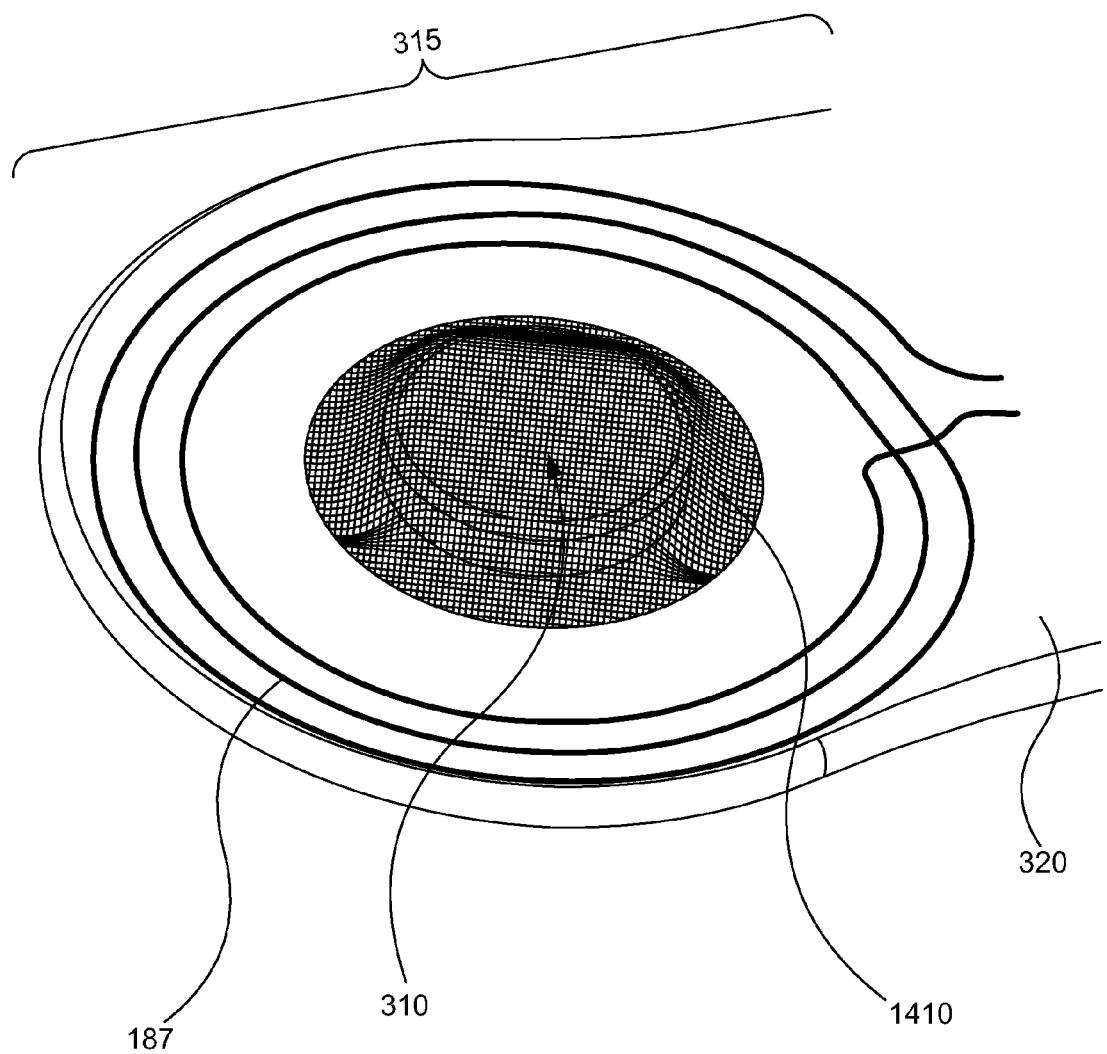
FIG. 14 is a perspective view of a first portion of a CI showing an embedded mesh, according to still another example of principles described herein.
Figure 15:
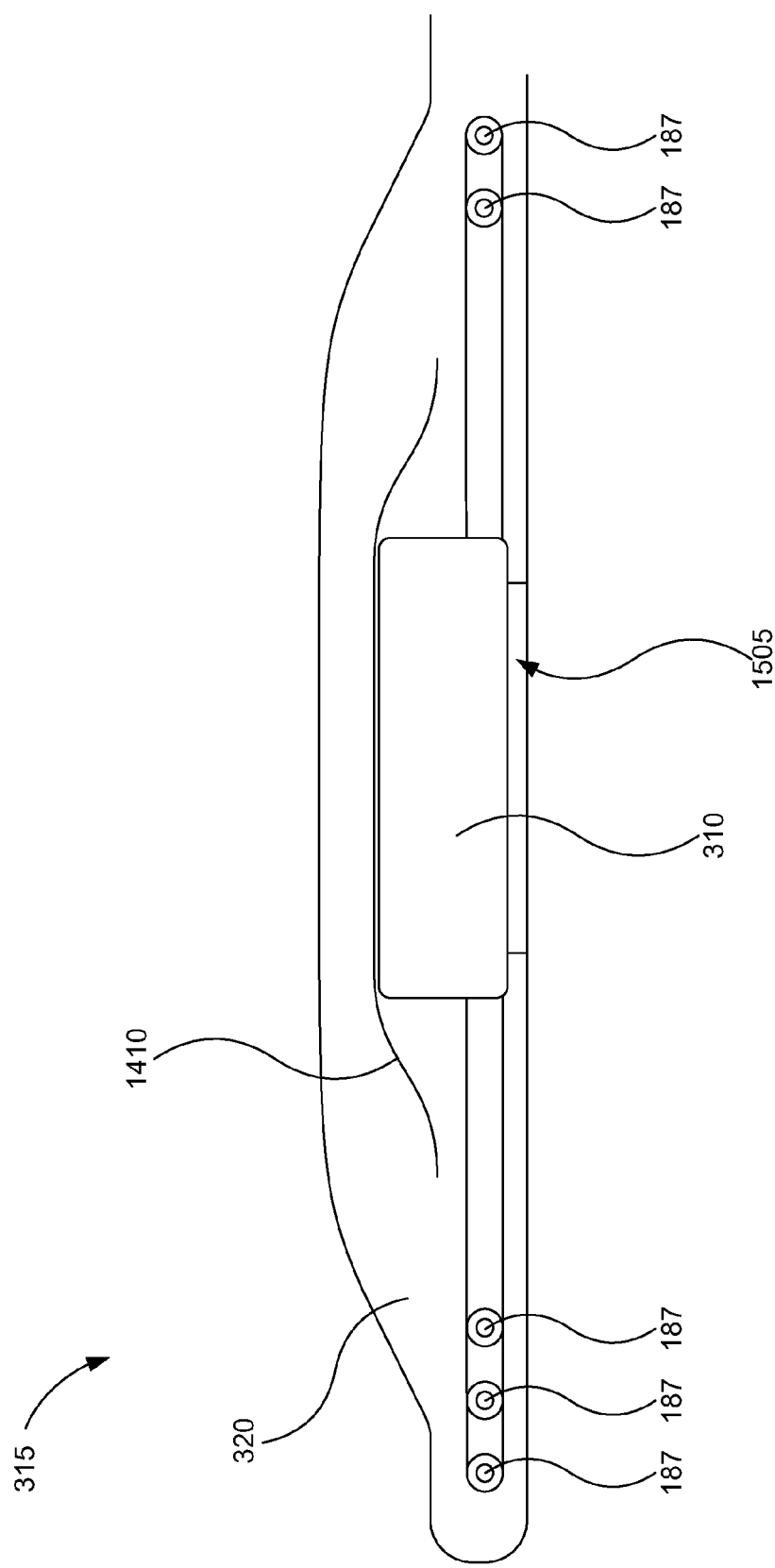
FIG. 15 is a cross-sectional diagram of the first portion of the CI depicting the embedded mesh of FIG. 14, according to still another example of principles described herein.

FIG. 14 is a perspective view of a first portion (315) of a cochlear implant (CI) (300) showing an embedded mesh (1410), according to still another example of principles described herein. FIG. 15 is a cross-sectional diagram of the first portion (315) of the CI (300) depicting the embedded mesh (1410) of FIG. 14. As depicted in FIGS. 14 and 15, the embedded mesh (1410) is embedded within the encapsulant (320) of the CI (300). In one example, the embedded mesh (1410) is embedded within the encapsulant (320) by molding the embedded mesh (1410) and a biocompatible magnet (310) or a magnet case (410, 1000) containing a magnet (310) as a subassembly. The embedded mesh (1410) is molded on the side of the magnet (310) closest to the outside of the user's body. The embedded mesh (1410) and biocompatible magnet (310) or a magnet case (410, 1000) containing a magnet (310) subassembly is then molded with other elements of the CI (300) through injection molding processes, and cured to form the encapsulant (320).

The embedded mesh (1410) is made of any mesh material or material that can be formed into a mesh. In one example, the embedded mesh (1410) is made of a thermoplastic polymer resin such as, for example, polyethylene terephthalate (PET) with the molecular formula $(C_{10}H_8O_4)_n$. PET may be commercially available from, for example, Invista North America S.A.R.L. Corp. and sold under the trademark DACRON®. Thus, the embedded mesh (1410) retains the magnet (310) in its original position, and keeps a biocompatible magnet (310) or a magnet case (410, 1000) containing a magnet (310) from flipping during MRI procedures that utilize magnetic fields of relatively lower strength.

However, when a user of a CI (300) is to be exposed to an MRI device that will produce magnetic fields of relatively higher strength, the magnet (310) can still be removed. The encapsulant (320) of FIGS. 14 and 15 includes an opening (1505). The opening (1505) is located at the underside of the encapsulant (320), and below the magnet (310). The underside of the CI (300) abuts the skull of the user once it is implanted. Therefore, the opening (1505) is accessible to a clinician after the clinician has surgically accessed the CI (300) and separated the CI (300) from the skull of the user. In this manner, a clinician can remove the magnet from the encapsulant (320) through the opening (1505) without destroying other portions of the CI (300).

In one example, the magnet (310) is hermetically sealed within a housing in a manner similar to the magnet cases (410, 1000) described above. In this example, the housing is made of titanium or a titanium alloy. In another example, the magnet is not hermetically sealed within a housing. In this example, the magnet comprises a biocompatible magnet.

Figure 16:
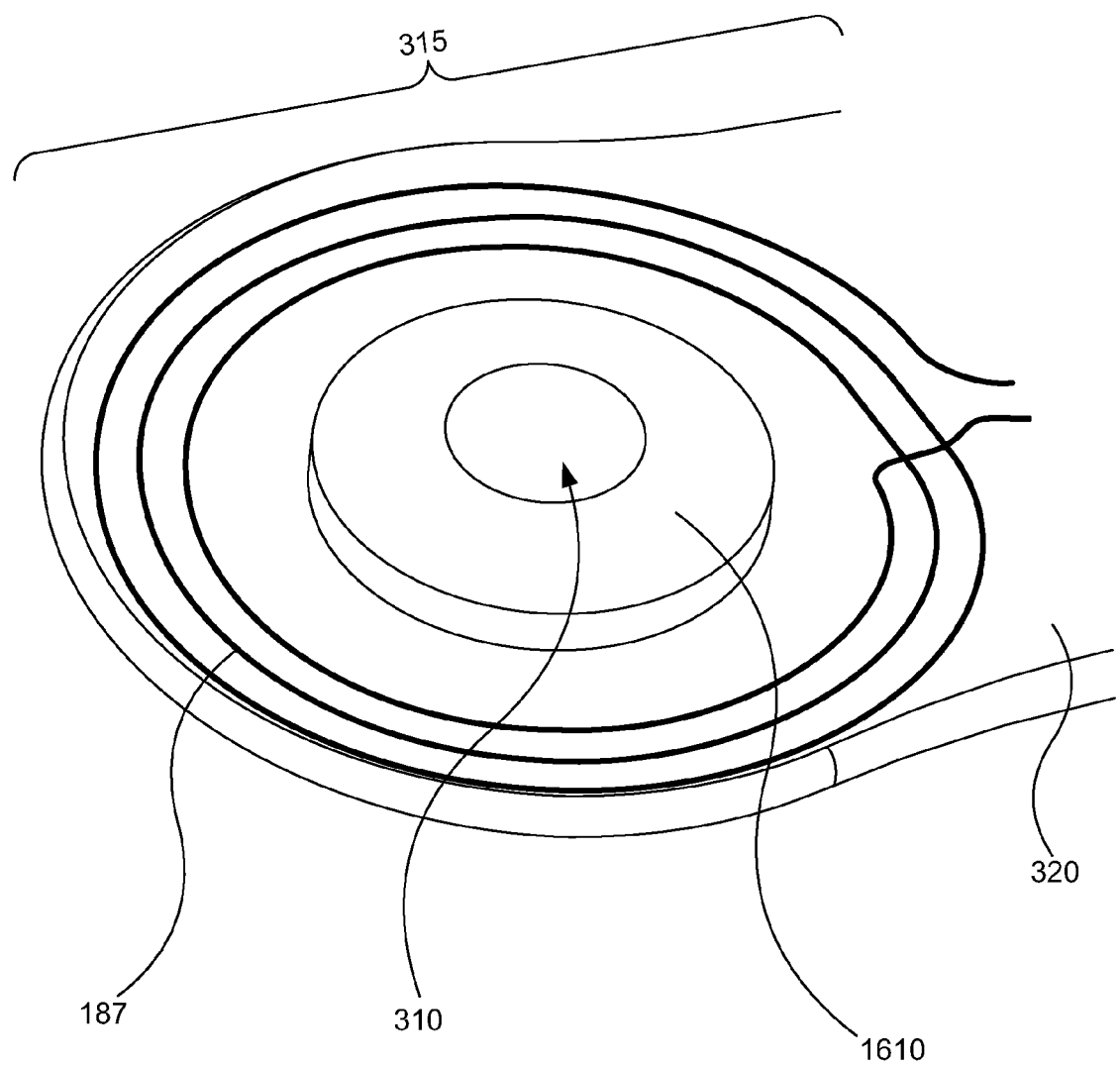
FIG. 16 is a perspective view of a first portion of a CI showing an embedded washer, according to still another example of principles described herein.
Figure 17:
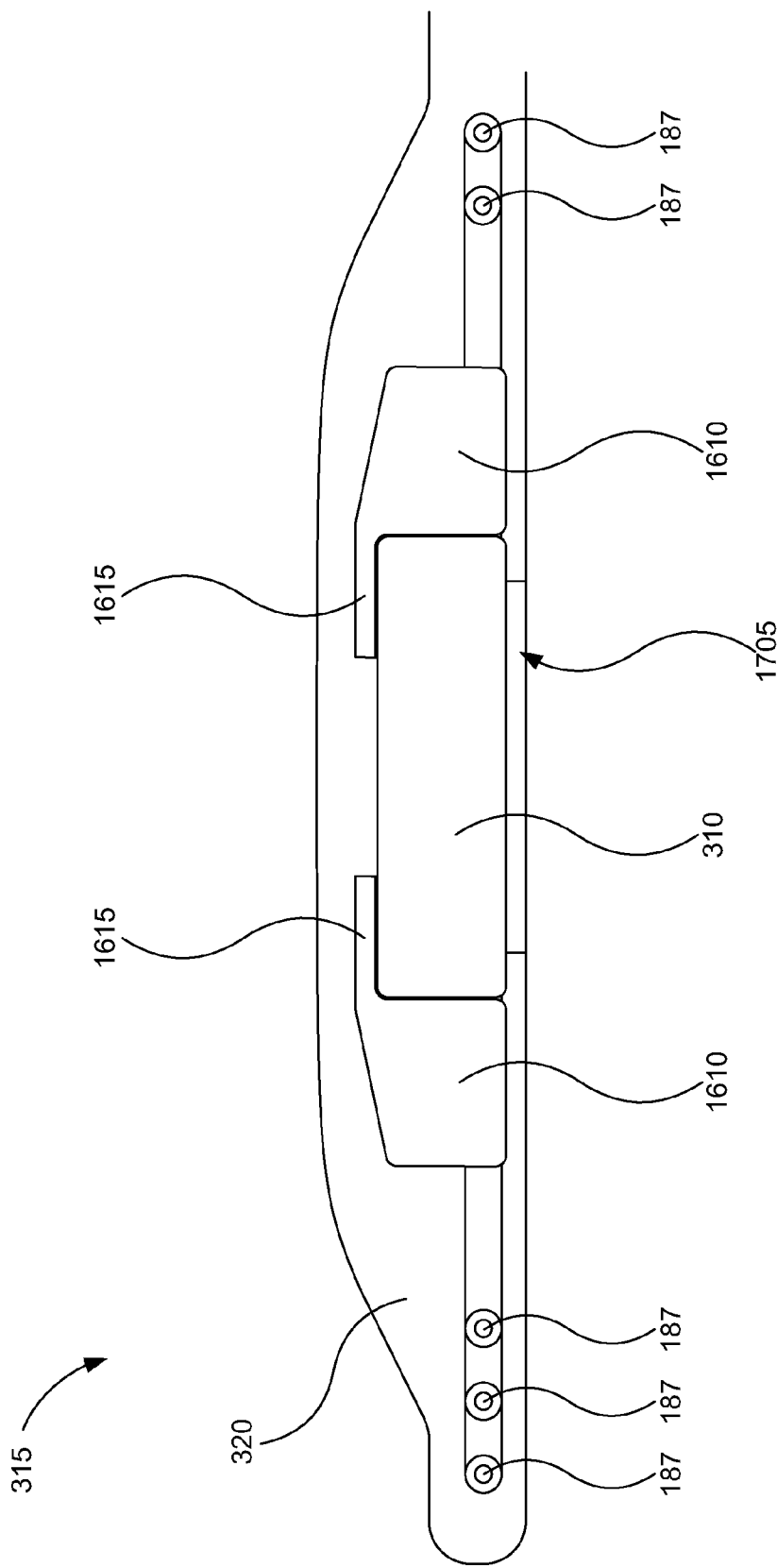
FIG. 17 is a cross-sectional diagram of the first portion of the CI depicting the embedded washer of FIG. 16, according to still another example of principles described herein.

Turning now to yet another example, FIG. 16 is a perspective view of a first portion (315) of a cochlear implant (CI) (300) showing an embedded washer (1610), according to still another example of principles described herein. FIG. 17 is a cross-sectional diagram of the first portion (315) of the CI (300) depicting the embedded washer (1610) of FIG. 16. As depicted in FIGS. 16 and 17, the washer (1610) is embedded within the encapsulant (320) of the CI (300). The process of embedding the washer (1610) within the encapsulant (320) is similar to the curing process of the silicone polymer described above. The washer (1610) is placed in the liquid silicone along with the antenna (187) and the magnet (310). The silicone is then cured, embedding these elements within the encapsulant (320).

The washer (1610) is made of any rigid material that can retain the magnet (310) within the CI (300). In one example, the washer (1610) is made of a thermoplastic polymer resin such as, for example, polyether ether ketone (PEEK). In still another example, the washer (1610) is made of a polysulfone. Thus, due to the increase in surface area of the washer (1610), the washer (1610) retains a biocompatible magnet (310) or a magnet case (410, 1000) containing a magnet (310) in its original position, and keeps the biocompatible magnet (310) or magnet case (410, 1000) containing a magnet (310) from flipping during MRI procedures that utilize magnetic fields of relatively lower strength. The washer (1610) comprises a flange (1615) that covers a portion of the magnet (310), and restricts movement of the magnet (310) in any direction.

However, as is the case of the example disclosed in connection with FIGS. 14 and 15, when a user of a cochlear implant (CI) (300) is to be exposed to an MRI device that will produce magnetic fields of relatively higher strength, the magnet (310) within the CI (300) of FIGS. 16 and 17 can still be removed. The encapsulant (320) of FIGS. 16 and 17 includes an opening (1705). The opening (1705) is located at the underside of the encapsulant (320), and below the magnet (310). As described above, the underside of the CI (300) abuts the skull of the user once it is implanted. Therefore, the opening (1705) is accessible to a clinician after the clinician has surgically accessed the CI (300) and separated the CI (300) from the skull of the user. In this manner, a clinician can remove the magnet from the encapsulant (320) through the opening (1705) without destroying other portions of the CI (300).

In one example, the magnet (310) is hermetically sealed within an encapsulant (320) in a manner similar to the magnet cases (410, 1000) described above. In this example, the encapsulant (320) is made of titanium or a titanium alloy. Hermetically sealing the magnet (310) in a housing prevents the magnet from interacting with human tissues while implanted in the user.

Figure 18:
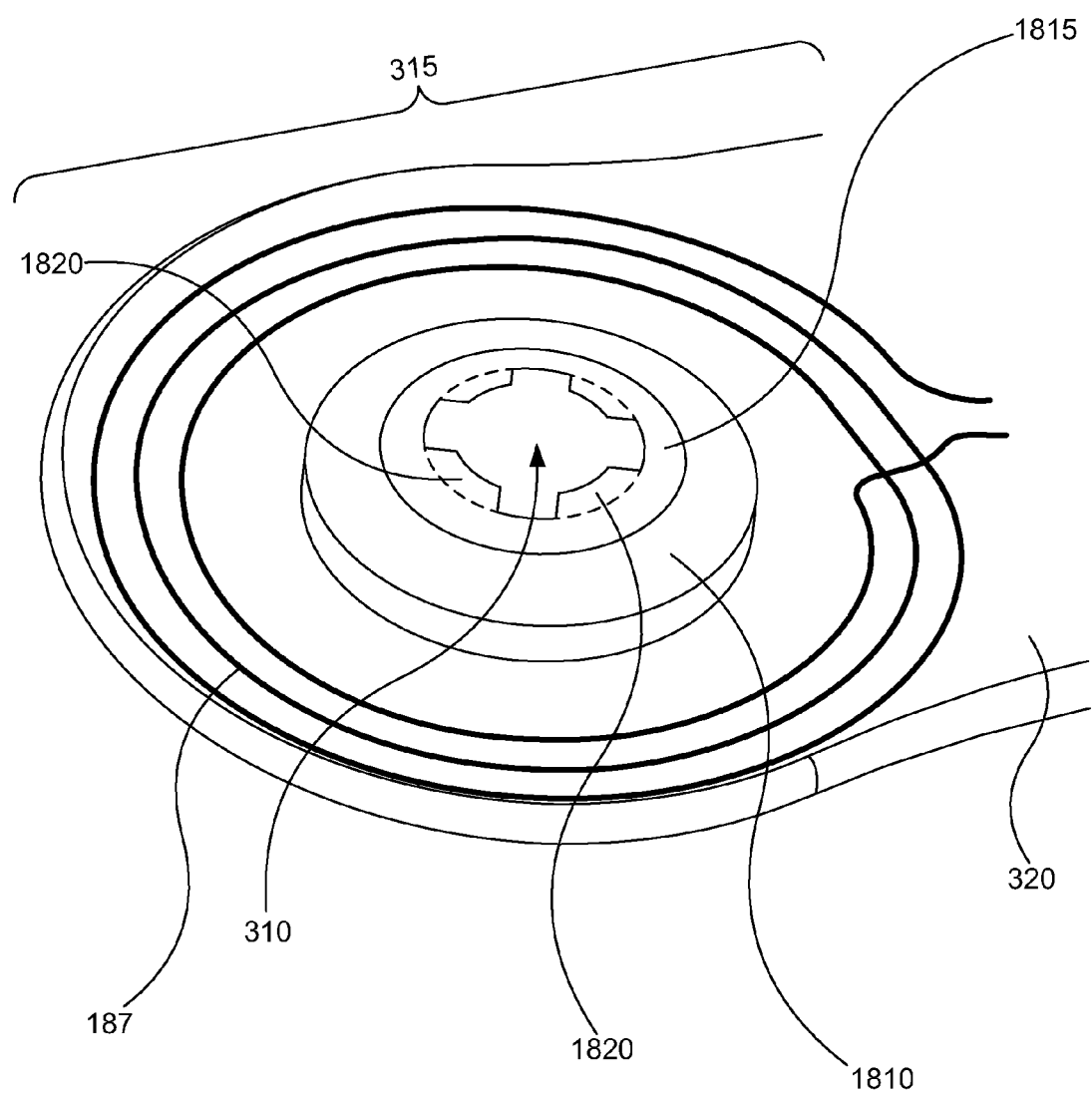
FIG. 18 is a perspective view of a first portion of a CI showing an embedded washer, according to still another example of principles described herein.
Figure 19:
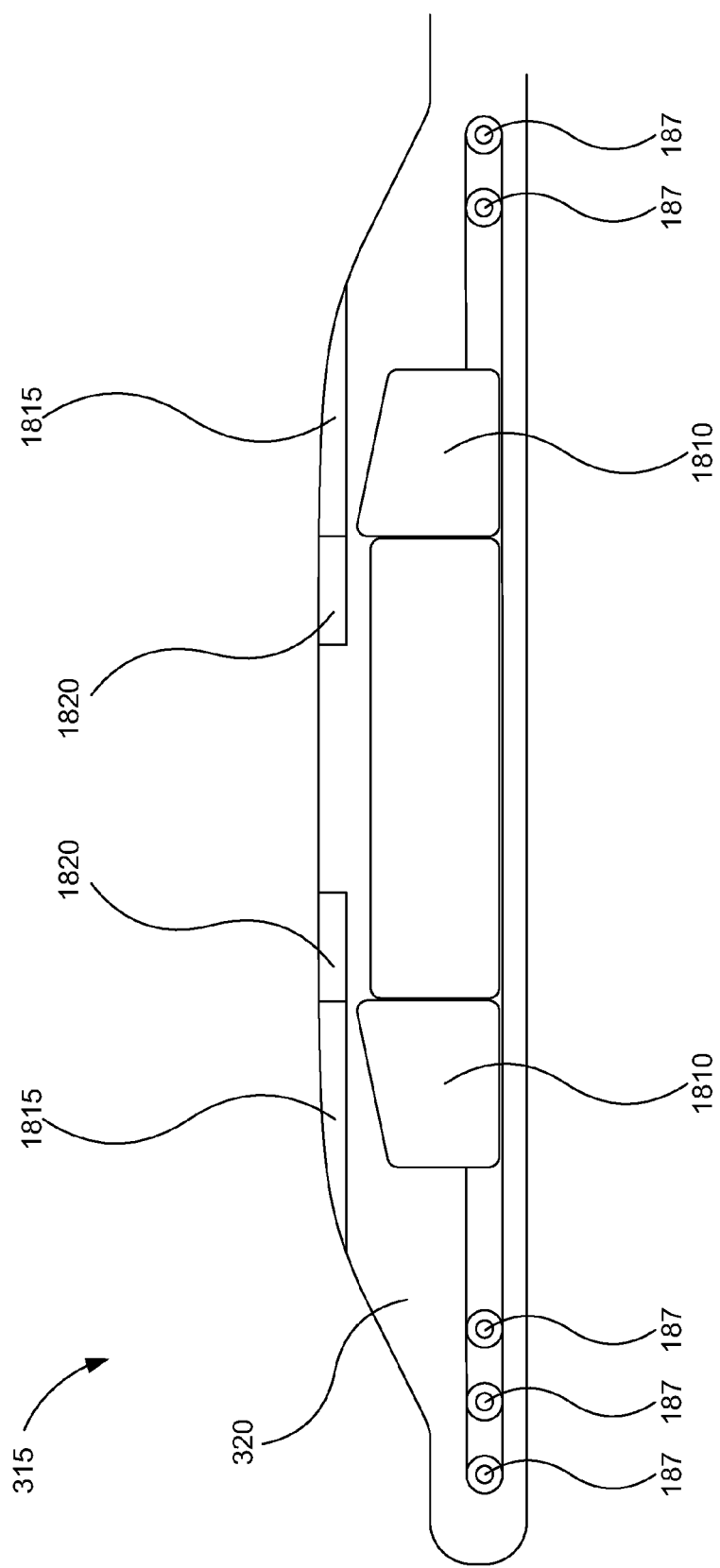
FIG. 19 is a cross-sectional diagram of the first portion of the CI depicting the embedded washer of FIG. 18, according to still another example of principles described herein.

FIG. 18 is a perspective view of a first portion (315) of a CI (300) showing an embedded washer (1810), according to still another example of principles described herein. FIG. 19 is a cross-sectional diagram of the first portion (315) of the CI (300) depicting the embedded washer (1810) of FIG. 18. As depicted in FIGS. 18 and 19, the washer (1810) is embedded within the encapsulant (320) of the CI (300). The process of embedding the washer (1810) within the encapsulant (320) is similar to the curing process of the silicone polymer described above. In one example, a core pin is inserted within the washer (1810) to keep the inner portion of the washer (1810) open so that it will later accommodate a biocompatible magnet (310) or a magnet case (410, 1000) containing a magnet (310). The washer (1810), with the core pin, is then inserted in a mold. Liquid silicone rubber (LSR) is injected into the mold through injection molding processes, and cured to form the encapsulant (320). Alternatively, other processes, such as transfer molding, compression molding, or casting, may be used. In one example, curing of the silicone is brought about by cross-linking the polymer chains of the polymerized silicone though the addition of a number of chemical additives, and exposure to ultraviolet radiation or heat.

As similarly described above in connection with the examples disclosed in FIGS. 16 and 17, the washer (1810) of FIGS. 18 and 19 is made of a rigid material that can retain the magnet (310) within the CI (300). In one example, the washer (1810) is made of a thermoplastic polymer resin such as, for example, polyether ether ketone (PEEK). In another example, the washer (1810) is made of a polysulfone. Again, due to the increase in surface area of the washer (1810), the washer (1810) retains a biocompatible magnet (310) or a magnet case (410, 1000) containing a magnet (310) in its original position, and keeps the biocompatible magnet (310) or magnet case (410, 1000) containing a magnet (310) from flipping during MRI procedures that utilize magnetic fields of relatively lower strength. Unlike the examples disclosed in FIGS. 16 and 17, the encapsulant (320) of FIGS. 18 and 19 does not have an opening located on the underside of the encapsulant (320). Therefore, if the magnet (310) is to be extracted, the encapsulant (320) provides for extraction of the magnet (310) through the top of the housing, (310) as will now be described in more detail.

When a user of the CI (300) is to be exposed to an MRI device that will produce magnetic fields of relatively higher strength, the magnet (310) within the CI (300) of FIGS. 18 and 19 can still be removed. As depicted in FIG. 18, the encapsulant (320) includes an overhang (1815) of the encapsulant (320) over the magnet (310) that secures the magnet (310) within the encapsulant (320). The overhang (1815) includes a number of flaps (1820) extending from the overhang (1815). The flaps (1820) assist in securing the magnet (310) in the encapsulant (320) during an MRI procedure of relatively lower strength, while providing a method of removing the magnet (310) from the encapsulant (320) for MRI procedures with a relatively high strength.

In order to remove the magnet (310) of FIGS. 18 and 19 when the user is to be exposed to the relatively higher magnetic field strengths, the clinician, after surgically accessing the CI (300), forces the flaps (1820) of the overhang (1815) apart to expose the washer (1810) and the magnet (310). The magnet (310) can then be separated from the washer (1810).

Figure 20:
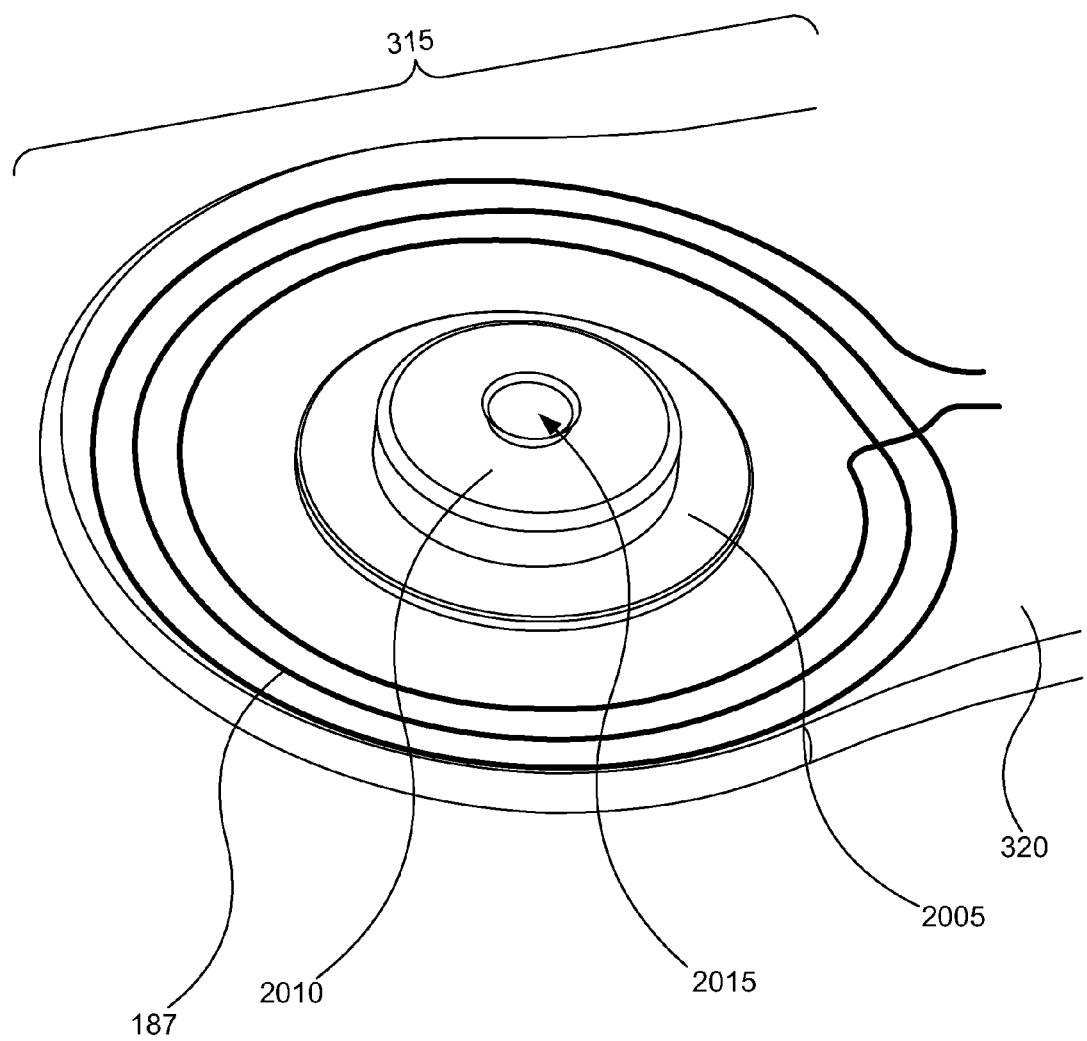
FIG. 20 is a perspective view of a first portion of the CI showing a retention ring, according to still another example of principles described herein.
Figure 21:
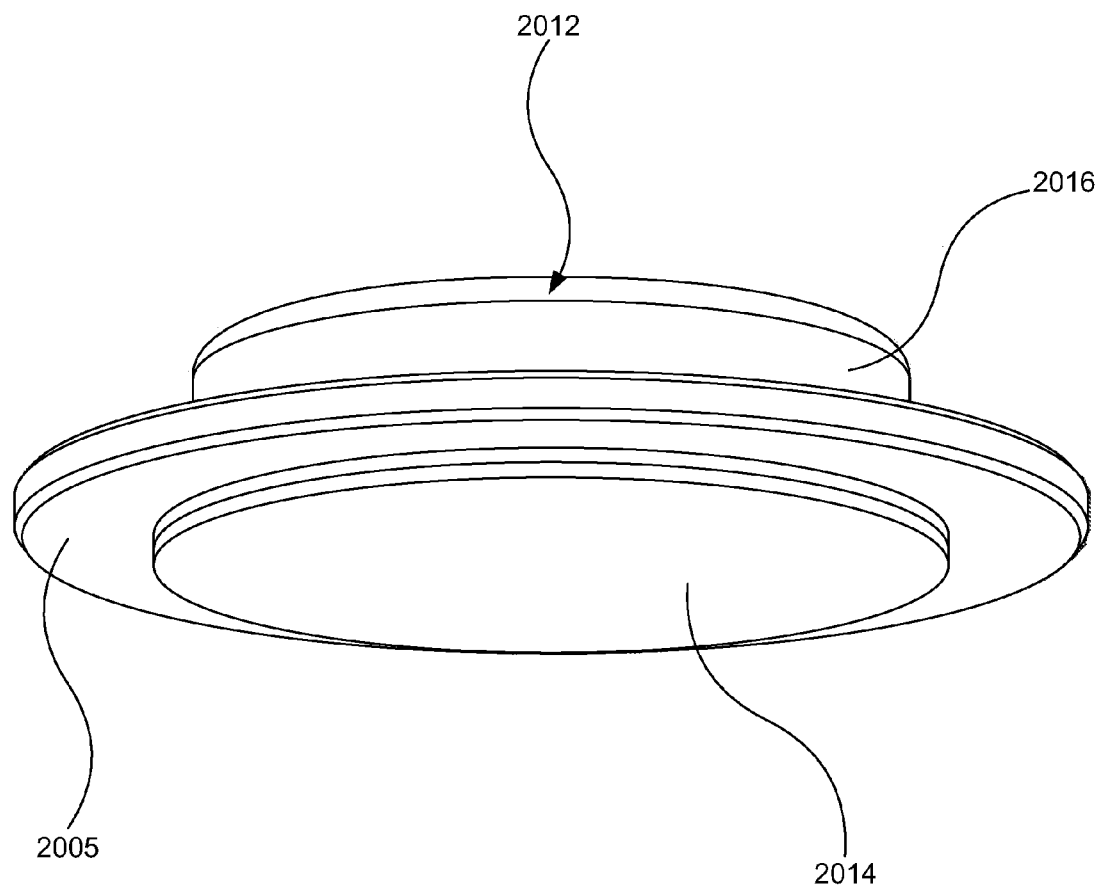
FIG. 21 is a perspective view of an assembled magnet case and retention ring of FIG. 20, according to still another example of principles described herein.
Figure 22:
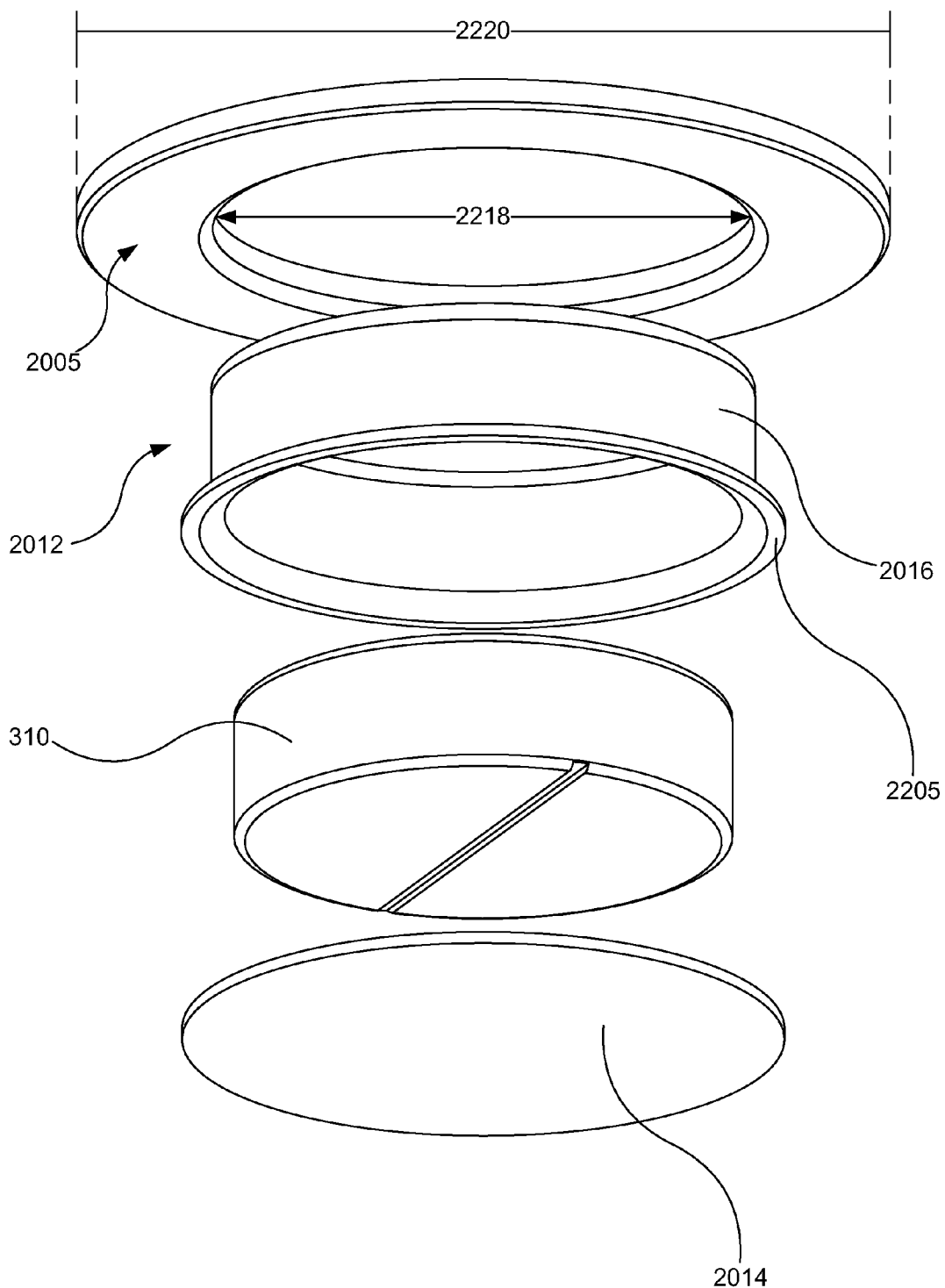
FIG. 22 is an exploded perspective view of the magnet case and retention ring of FIG. 21, according to still another example of principles described herein.
Figure 23:
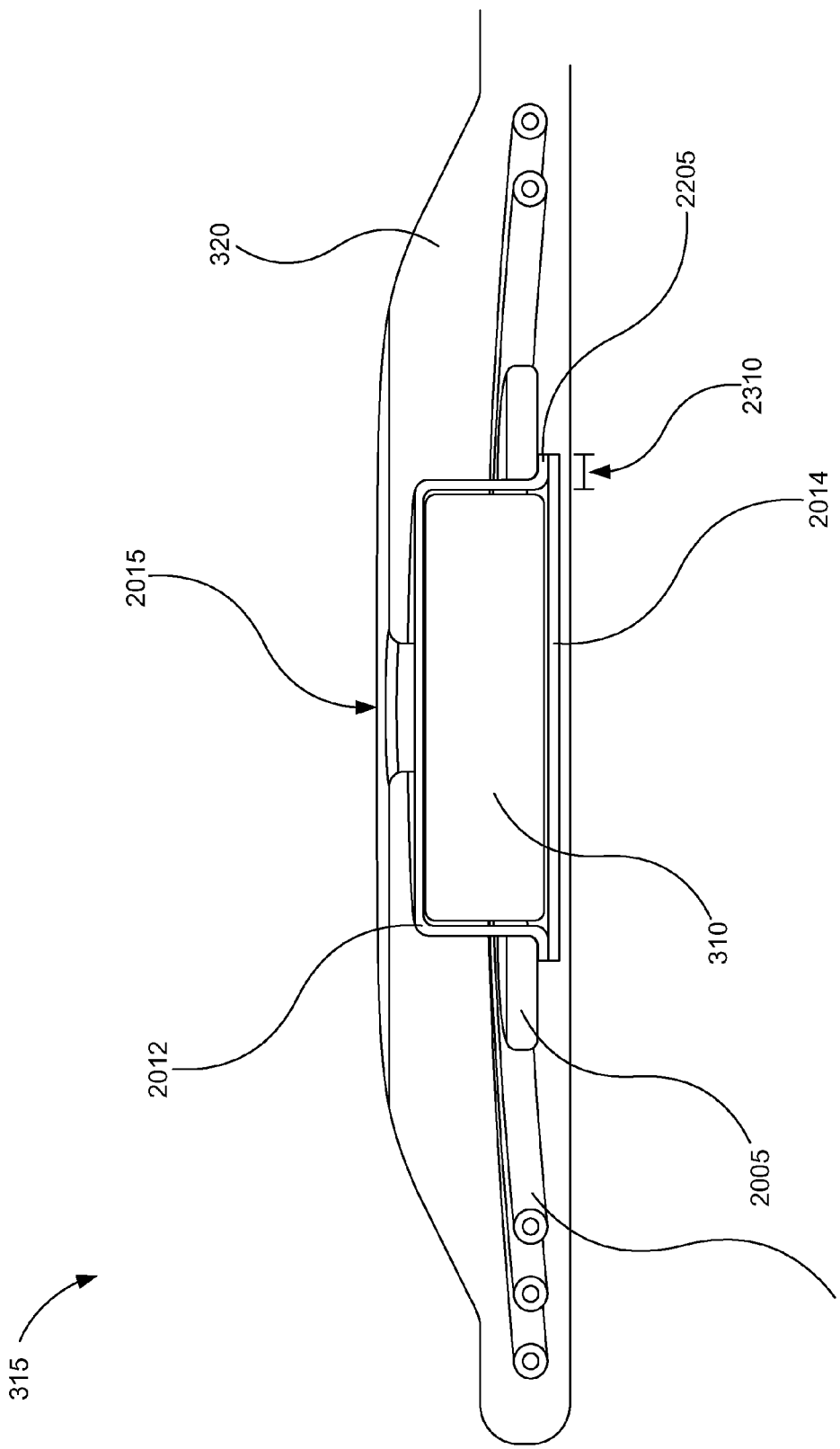
FIG. 23 is a cross-sectional diagram of the first portion of the CI depicting the magnet case and retention ring of FIG. 21, according to still another example of principles described herein.

FIG. 20 is a perspective view of a first portion (315) of the CI (300) showing a retention ring (2005), according to still another example of principles described herein. FIG. 21 is a perspective view of an assembled magnet case (2010) and retention ring (2005) of FIG. 20. FIG. 22 is an exploded perspective view of the magnet case (2010) and retention ring (2005) of FIG. 21. FIG. 23 is a cross-sectional diagram of the first portion (315) of the CI (300) depicting the magnet case (2010) and retention ring (2005) of FIG. 21. As depicted in FIGS. 20 through 23, the magnet case (2010) hermetically seals the magnet (310) therein, and is held stationary within the first portion (315) of the CI (300) by the retention ring (2005).

The magnet case (2010) comprises a cover (2014) and a top enclosure (2012) that, when coupled together, form the magnet case (2010). In one example, the top enclosure (2012) and a cover (2014) are laser beam welded to hermetically seal the magnet (310). The cover (2014) and a top enclosure (2012) are made of a material that does not react with human tissues such as, for example, titanium. In one example, the top enclosure (2012) of the magnet case (2010) is made from deep-drawn titanium. In another example, the top enclosure (2012) is formed by machining a solid bar of titanium.

As depicted in FIGS. 22 and 23, the top enclosure (2012) comprises a flange (2205) that is approximately perpendicular with respect to a side wall (2016) of the top enclosure (2012). The flange (2205) extends from the center axis of the top enclosure (2012) at a distance (2310) such that the total diameter of the top enclosure (2012) is approximately equal to the diameter of the cover (2014). In this manner, the surface of the top enclosure (2012) formed by the flange (2205) abuts a portion of the cover (2014), and provides a point at which a weld between the top enclosure (2012) and the cover (2014) may be formed.

In one example, the retention ring (2005) of FIGS. 20 through 23 is made of a thermoplastic material such as, for example, polyether ether ketone (PEEK), a polysulfone, or polytetrafluoroethylene (PTFE). The retention ring (2005) has an internal bore (2218) that is approximately equal to the diameter of the top enclosure (2012) at the side wall (2016). Because the flange (2205) of the top enclosure (2012) has a wider diameter relative to the internal bore (2218) of the retention ring (2005), the flange (2205) prevents the magnet case (2010) and enclosed magnet (310) from separating from the CI (300) or flipping relative to the CI (300).

The external diameter (2220) of the retention ring (2005) is small enough to fit within the diameter of the antenna (187), but large enough to anchor the magnet case (2010) to the encapsulant (320). In one example, the external diameter (2220) of the retention ring (2005) is approximately between 12 and 18 mm.

In one example, the first portion (315) of the CI (300) of FIGS. 20-24 further comprises a pressure equalizing hole (2015). The pressure equalizing hole (2015) allows for pressure buildup within the CI (300) to be alleviated. For example, when the external components (200) of the CI (300) are removed from and reattached to the user's head, the pocket defined within the first portion (315) of the CI (300), and in which encloses the magnet case (2010) and retention ring (2005), can become inflated with gases. For example, when the external components (200) of the CI (300) are removed, a vacuum is created within the pocket defined within the first portion (315) of the CI (300). This can cause discomfort, or, in extreme circumstances, may cause the pocket to rupture, and expose one or more of the elements of the CI (300) to become exposed to fluids and tissues surrounding the CI (300). Thus, the pressure equalizing hole (2015) allows for gases to move in and out of the pocket defined within the first portion (315) of the CI (300) freely. The various examples described herein may incorporate a pressure equalizing hole (2015) in a similar manner as demonstrated in the examples of FIGS. 20 through 24.

Figure 24:
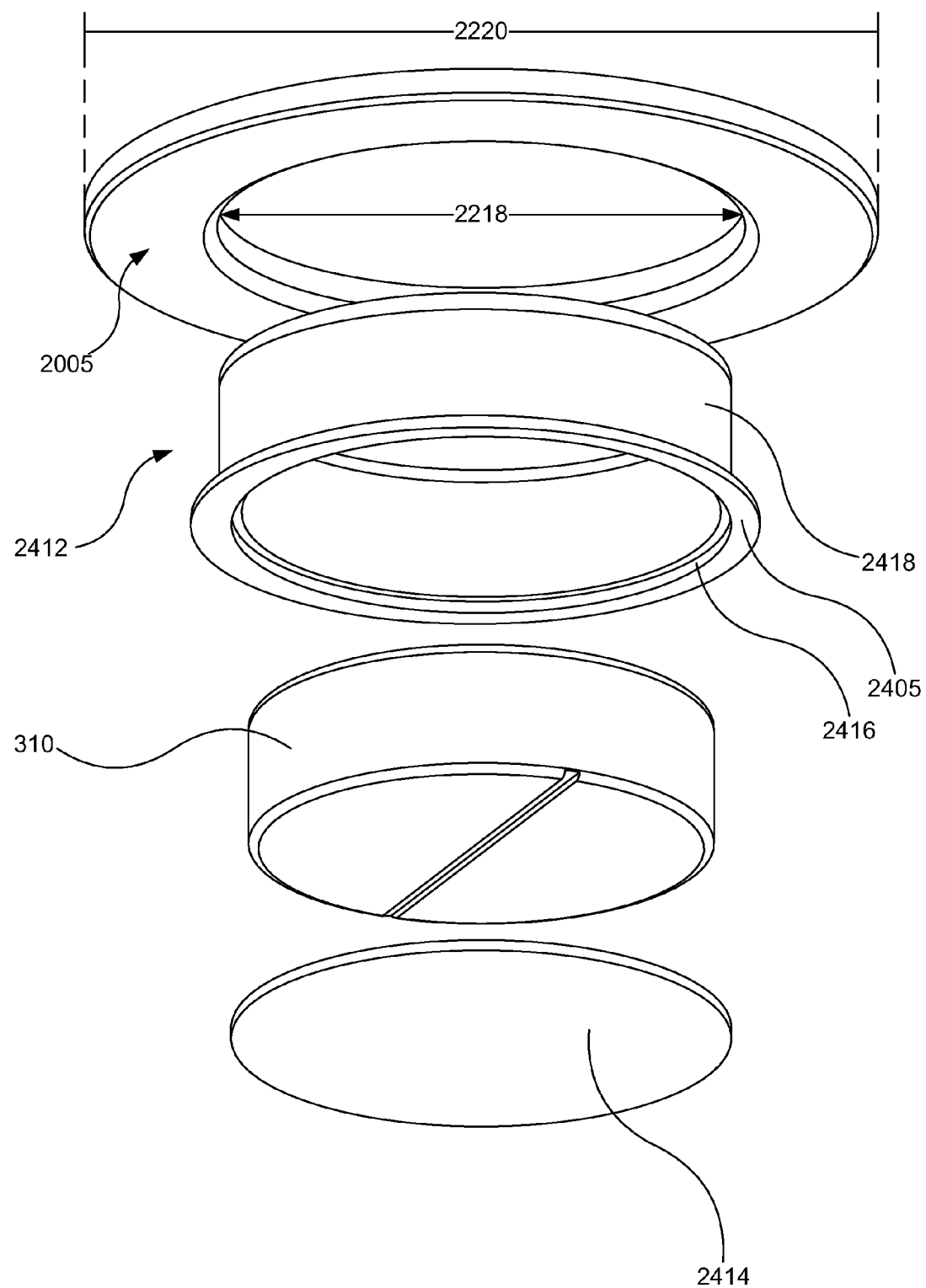
FIG. 24 is an exploded perspective view of the magnet case and retention ring of FIG. 20, according to still yet another example of principles described herein.
Figure 25:
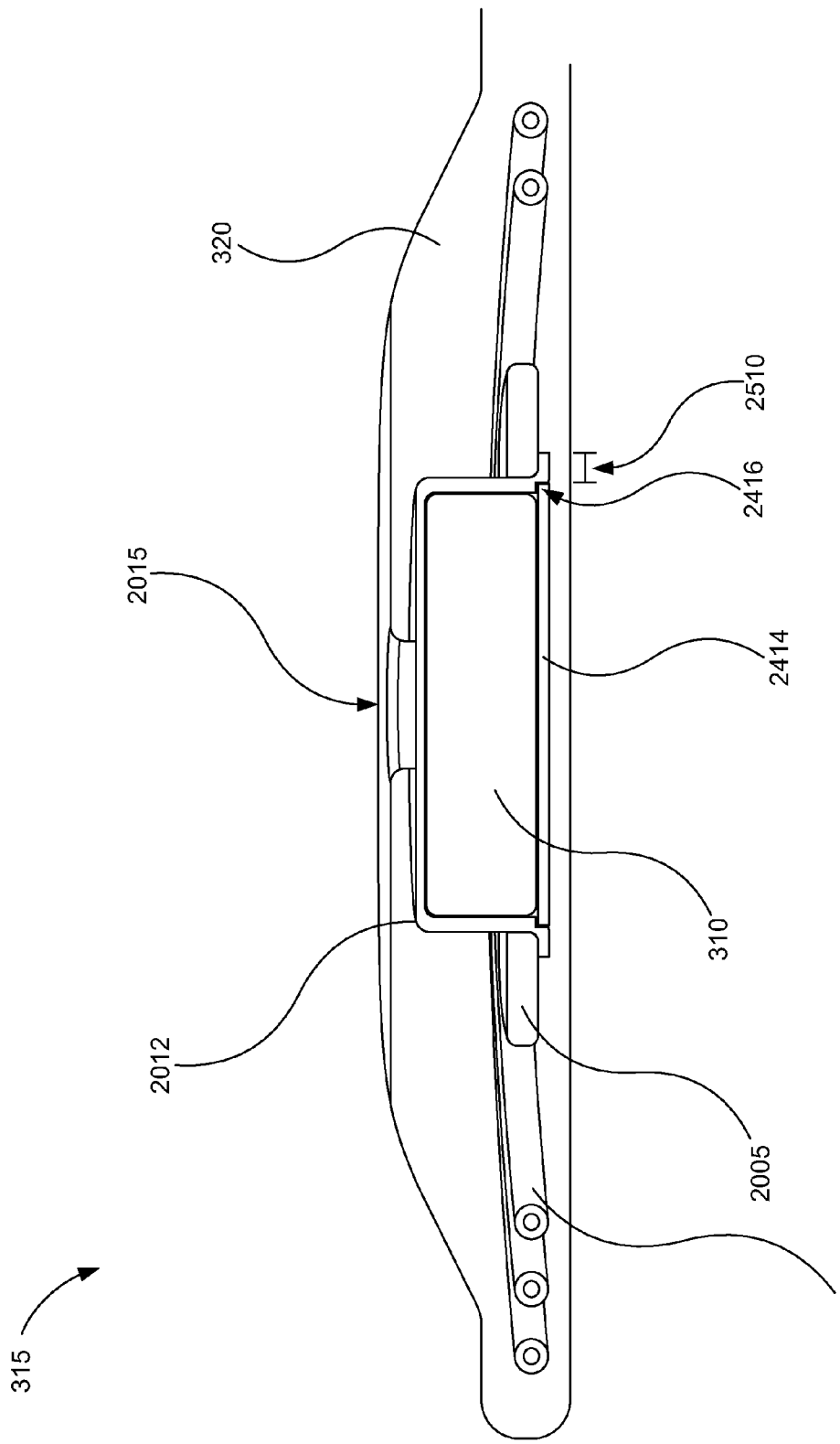
FIG. 25 is a cross-sectional diagram of the first portion of the CI depicting the magnet case and retention ring of FIG. 24, according to still another example of principles described herein.

Turning now to FIGS. 24 and 25 specifically, an exploded perspective view of the magnet case (2010) and the retention ring (2005) of FIG. 20, according to still yet another example of principles described herein is depicted. FIG. 25 is a cross-sectional diagram of the first portion (310) of the CI depicting the magnet case (2010) and retention ring (2005) of FIG. 24, according to still another example of principles described herein. The magnet case (2010) comprises a cover (2414) and a top enclosure (2412) that, when coupled together, form the magnet case (2010). In one example, the top enclosure (2412) and a cover (2414) are laser beam welded to hermetically seal the magnet (310).

The cover (2414) and top enclosure (2412) are made of a material that does not react with human tissues such as, for example, titanium. In one example, the top enclosure (2412) of the magnet case (2010) is formed by machining a solid bar of titanium. In another example, the top enclosure (2412) is made from deep-drawn titanium.

As depicted in FIGS. 24 and 25, the top enclosure (2012) comprises a flange (2405) that is approximately perpendicular with respect to a side wall (2416) of the top enclosure (2412). The flange (2405) extends from the center axis of the top enclosure (2412) at a distance (2510). In this example, the top enclosure (2412) of the magnet case (2010) is different from the top enclosure (2012) of FIGS. 21 through 23 in that it includes a recess (2416) defined within the top enclosure (2412). The recess (2416) is sized such that the cover (2414) fits within the recess (2416) and can be coupled to the top enclosure (2412).

In one example, the retention ring (2005) of FIGS. 24 and 25 is made of a thermoplastic material such as, for example, polyether ether ketone (PEEK) or a polysulfone or polytetrafluoroethylene (PTFE). The retention ring (2005) has an internal bore (2218) that is approximately equal to the diameter of the top enclosure (2412) at the side wall (2418). Because the flange (2405) of the top enclosure (2412) has a wider diameter relative to the internal bore (2218) of the retention ring (2005), the flange (2405) prevents the magnet case (2010) and enclosed magnet (310) from separating from the CI (300) or flipping relative to the CI (300). The examples of FIGS. 20 through 25 provide for the retention of the magnet (310) within the CI (300) during low power MRI procedures.

Throughout the present disclosure, several apparatus have been disclosed that retain a magnet within a CI during an MRI procedure. Throughout these examples, various methods may be employed for performing an MRI procedure without removal of the magnet from the CI. In one example, a clinician performs a relatively low-powered MRI procedure on the patient while one of the examples of a magnet retention system is utilized. In another example, additional apparatus may be used in conjunction with the above examples of magnet retention apparatus. In this example, a clinician may assist the retention of the magnet within the CI by securing a compression bandage or similar device to the area of the patients head containing the CI.

Further, the various examples of CI systems described above provide for apparatus for retaining a magnet within a cochlear implant. Throughout these examples, various methods may be employed to remove the magnet from the CI system, and replace the magnet. In one example, a clinician may surgically access the cochlear implant. Upon gaining access to the CI, the magnet may be removed. An MRI procedure may then be performed on the patient from whose body the magnet was removed. After performing the MRI procedure, the magnet may be replaced.

The specification and figures describe systems and methods for retaining a magnet in a cochlear implant. The system comprises a retainer embedded within a housing of the cochlear implant, and a magnet case removably engaged with the retainer. The various systems and methods may have a number of advantages, including, for example: 1) retention of the magnet within the cochlear implant during a low strength MRI procedure; and 2) disengagement of the magnet within the cochlear implant during a high strength MRI procedure that includes minor surgery to be performed on a user of the cochlear implant.

The preceding description has been presented to illustrate and describe examples of the principles described. This description is not intended to be exhaustive or to limit these principles to any precise form disclosed. Many modifications and variations are possible in light of the above teaching.

What is claimed is:

1. A system for retaining a magnet in a cochlear implant, comprising:
 a retainer embedded within an encapsulant of the cochlear implant, the retainer comprising an outer ring, an inner ring, and supporting buttresses between the inner and outer rings, with encapsulant disposed between the inner and outer rings to secure the retainer in the encapsulant; and
 a magnet case releasably engaged with the retainer, the inner ring configured to receive the magnet case, a magnet disposed within the magnet case.

2. The system of claim 1, in which the system further comprises:
 a number of first threads formed on an internal side of the inner ring; and
 a number of second threads formed on the magnet case, the second threads formed on the magnet case mating with the first threads formed on the retainer,
 in which the magnet case is engaged with the retainer via mating of the first threads with the second threads.

3. The system of claim 1, in which a spring in the encapsulant imparts a spring force against the magnet case when the magnet case is engaged with the retainer.

4. The system of claim 1, in which the encapsulant is made of a polysiloxane.

5. The system of claim 1, in which the retainer comprises:
 a washer comprising a flange, the flange covering at last two surfaces of the magnet case, the washer restricting movement of the magnet case within the cochlear implant housing.

6. The system of claim 5, in which the encapsulant defines an opening in the side of the encapsulant that abuts a skull of a user of the cochlear implant,
 in which the magnet case is removed from the encapsulant via the opening.

7. The system of claim 5, in which the retainer comprises:
 a washer;
 an overhang formed in the encapsulant; and
 a number of flaps extending from the overhang,
 in which the washer restricts rotation of the magnet case within the cochlear implant and the overhang and flaps retain the magnet case within the cochlear implant.

8. The system of claim 1, in which the retainer comprises:
 a retention ring; and
 a flange formed on a top enclosure of the magnet case;
 in which the flange of the top enclosure has a wider diameter relative to a diameter of an internal bore of the retention ring.

9. The system of claim 1, in which the retainer is made of a thermoplastic material comprising polyether ether ketone (PEEK), a polysulfone (PSF), PEAK, or combinations thereof.

10. The system of claim 1, in which the magnet case comprises titanium or a titanium alloy and in which the magnet case hermetically seals a magnet.

11. The system of claim 1, in which the encapsulant is made of silicone.

12. The system of claim 1, further comprising a tool for removing the magnet case from a magnet retainer, in which the tool comprises:
 a handle; and
 an extraction bit coupled to the handle via a shaft,
 in which the extraction bit is shaped to mate with an extraction cavity defined within the magnet case.

13. The system of claim 1, further comprising a pressure equalizing hole that allows gasses to move in and out of the cochlear implant.

14. A system for retaining a magnet in a cochlear implant, comprising:
 a retainer embedded within an encapsulant of the cochlear implant;
 a magnet case engaged with the retainer;
 an inner ring formed in the retainer, the inner ring defining a void in the retainer;
 a number of protrusions formed on an internal side of the inner ring, the number of protrusions defining a number of notches therein;
 a number of wings formed on the magnet case; and
 a number of detents formed on the wings, the detents mating with the protrusions when the magnet case is engaged with the retainer.

15. The system of claim 14, further comprising a number of spaces along the inner ring at which a protrusion is not formed, the spaces allowing the wings to pass between the protrusions.

16. The system of claim 14, further comprising a spring force interposed between the encapsulant and the magnet case, in which the spring force imparts a force against the magnet case when the magnet case is engaged with the retainer.

17. A system for retaining a magnet in a cochlear implant, comprising:
 a retainer embedded within an encapsulant of the cochlear implant; and
 a magnet case engaged with the retainer;
 in which the retainer comprises:
 a first outer ring;
 a second outer ring;
 a first inner ring;
 a second inner ring;
 a number of rib sections coupling the first outer ring to the first inner ring and the second outer ring to the second inner ring;
 a number of inner braces that couple the first inner ring to the second inner ring;
 a number of outer braces that couple the first outer ring to the second outer ring;
 a number of break points located between the first outer ring and the first inner ring and between the second outer ring and the second inner ring; and
 a magnet retention ring coupled to the second inner ring via a number of retention ring supports.

18. The system of claim 17, in which the magnet case is removable from the retainer by breaking the retainer at the break points.

19. A system for retaining a magnet in a cochlear implant, comprising:
- a retainer embedded within an encapsulant of the cochlear implant; and
- a magnet case engaged with the retainer;
- in which the retainer comprises:
  - an embedded mesh located between a side of the cochlear implant closest to the outside of a user's body and the magnet.

20. The system of claim 19, in which the encapsulant defines an opening in the side of the encapsulant that abuts a skull of a user of the cochlear implant,
- in which the magnet case is deteachable from the encapsulant via the opening.

21. A method of making the system of claim 1, comprising embedding a magnet retainer within an encapsulant of a cochlear implant by:
- positioning the retainer in a mold;
- injecting a polymer into the mold; and
- curing the polymer to form the encapsulant.

22. The method of claim 21, in which the polymer is a polysiloxane.

23. The method of claim 21, further comprising engaging the magnet retainer with the encapsulant before curing the polymer.

24. A retainer for retaining a magnet within a cochlear implant comprising:
- a number of first fasteners that couple with a number of corresponding second fasteners of a magnet case hermetically sealing the magnet;
- a number of supports, supporting the first fasteners, embedded within an encapsulant of the cochlear implant; and
- a spring embedded in the encapsulant at a bottom of the retainer for applying a spring force on the magnet case when in the retainer.

25. The retainer of claim 24, in which the number of fasteners comprises a number of screw threads, a number of protrusions including a number of notches that mate with a number of detents of a number of wings of the magnet case, a number of rib sections, a magnet retention ring, a mesh, a washer, or a combinations thereof.

* * * * *